United States Patent
Cummings et al.

(10) Patent No.: US 9,572,864 B2
(45) Date of Patent: Feb. 21, 2017

(54) COMPOSITIONS AND USES OF LECTINS

(71) Applicant: Emory University, Atlanta, GA (US)

(72) Inventors: Richard D. Cummings, Atlanta, GA (US); Sean R. Stowell, Decatur, GA (US); Connie Arthur, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/966,941

(22) Filed: Dec. 11, 2015

(65) Prior Publication Data

US 2016/0175394 A1  Jun. 23, 2016

Related U.S. Application Data

(63) Continuation of application No. 13/577,446, filed as application No. PCT/US2011/024497 on Feb. 11, 2011, now abandoned.

(60) Provisional application No. 61/303,733, filed on Feb. 12, 2010.

(51) Int. Cl.
*A61K 38/00* (2006.01)
*A61K 45/06* (2006.01)
*A61K 38/17* (2006.01)

(52) U.S. Cl.
CPC ......... *A61K 38/1732* (2013.01); *A61K 38/178* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,585,254 A | 12/1996 | Maxwell et al. | |
| 6,159,174 A | 12/2000 | Oldham et al. | |
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 6,967,021 B2* | 11/2005 | Panjwani | A61K 38/1709 424/185.1 |
| 7,135,552 B2 | 11/2006 | Fujisaki et al. | |
| 2003/0109464 A1 | 6/2003 | Huflejt et al. | |
| 2007/0269833 A1 | 11/2007 | Minamisawa et al. | |
| 2008/0044385 A1* | 2/2008 | Nishi | C07K 14/4726 424/93.2 |
| 2008/0113907 A1 | 5/2008 | Rosewicz et al. | |

FOREIGN PATENT DOCUMENTS

| | | |
|---|---|---|
| CN | 101007852 | 8/2007 |
| EP | 1736541 | 1/2013 |
| WO | 00/69894 | 11/2000 |
| WO | 2007/018229 | 2/2007 |

OTHER PUBLICATIONS

Blixt et al. "Printed covalent glycan array for ligand profiling of diverse glycan binding proteins.", Proceedings of the National Academy of Sciences of the United States of America, 2004; 101(49): 17033-17038.
Cash et al. "Symbiotic Bacteria Direct Expression of an Intestinal Bactericidal Lectin.", Science, 2006; 313(5790): 1126-1130.
Kohatsu et al. "Galectin-3 Induces Death of Candida Species Expressing Specific β-1,2-Linked Mannans.", The Journal of Immunology, 2006; 177(7): 4718-4726.
Miller et al. "Discovery of novel antibacterials" Expert Opin. Drug Discov., 2010; 5(2):145-154.
Nagy-Agren et al. "Management of Infections in Palliative Car Patients with Advanced Cancer" Journal of Pain and Symptom Management, 2002; 24(1 ): 64-70.
NIH, Antimicrobial (Drug) Resistance, 2012, available at http://www.niaid.nih.gov/topics/antimicrobialresistance/examples/.
Pettersson et al. "Ribavirin treatment effects on breast canccers overexpressing eIF4E, a biomarker with prognostic specificity for luminal B-type breast cancer" Clin. Cancer Res., 17(9): 2874-2884.
Rabinovich et al. "Galectins as immunoregulators during infectious processes: from microbial invasion to the resolution of the disease" Parasite Immunology, 2005; 27: 103-114.
Rowe et al. "Blood group O protects against severe Plasmodium falciparum malaria through the mechanism of reduced rosetting" Proceedings of the National Academy of Sciences, 2007; 104(44): 17471-17476.
Springer et al. "Blood group isoantibody stimulation in man by feeding blood group-active bacteria." The Journal of Clinical Investigation, 1969; 48(7): 1280-1291.
Stowell et al. "Galectin-1, -2, and -3 Exhibit Differential Recognition of Sialylated Glycans and Blood Group Antigens." Journal of Biological Chemistry, 2008; 283(15): 10109-10123.
Stowell et al. "Dimeric Galectin-8 Induces Phosphatidylserine Exposure in Leukocytes through Polylactosamine Recognition by the C-terminal Domain." 2008; Journal of Biological Chemistry, 283(29): 20547-20559.
Stowell et al. "Galectin-1 Induces Reversible Phosphatidylserine Exposure at the Plasma Membrane." Molecular Biology of the Cell, 2009; 20(5): 1408-1418.
Stowell et al. "Innate immune lectins kill bacteria expressing blood group antigen" Nature Medicine, 2010; 6(3), 295-302.
Thiel et al. "A second serine protease associated with mannan-binding lectin that activates complement." Nature, 1997; 386(6624): 506-510.

(Continued)

*Primary Examiner* — Gary Nickol
*Assistant Examiner* — Mary Lyons
(74) *Attorney, Agent, or Firm* — Emory Patent Group

(57) ABSTRACT

The disclosure relates to uses of a purified or isolated lectin to kill bacteria, viruses, and other pathogens. In certain embodiments, the disclosure relates to method of treating or preventing an infection comprising administering a purified or isolated galectin to a subject in need thereof. In certain embodiments, the subject is at risk of, exhibiting symptoms of, or diagnosed with a pathogenic infection.

2 Claims, 42 Drawing Sheets

(56) References Cited

OTHER PUBLICATIONS

Vasta "Roles of galectins in infection." Nat Rev Micro, 2009; 7(6): 424-438.
Wittels et al. "Blood group incidence and *Escherichia coli* bacterial sepsis" Transfusion, 1986; 26(6): 533-535.
Extended European Search Report for EP Application No. 11742853.2, dated Oct. 9, 2013.

* cited by examiner e f

COMPOSITIONS AND USES OF LECTINS

CROSS REFERENCE TO RELATED APPLICATIONS

This application is a continuation of pending U.S. patent application Ser. No. 13/577,446 filed Aug. 7, 2012 which is a 371 National Stage Application of PCT Application PCT/US11/24497 filed Feb. 11, 2011 and claims priority to U.S. Provisional Application No. 61/303,733 filed Feb. 12, 2010, all hereby incorporated by reference in their entirety.

ACKNOWLEDGEMENTS

This invention was made with government support under Grants RO1 HL-85607 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 10082USCON_ST25.txt. The text file is 11 KB, was created on Dec. 11, 2015, and is being submitted electronically via EFS-Web.

BACKGROUND

Blood type is a classification of blood based on the presence or absence of inherited antigenic substances on the exterior surface of red blood cells. The A and B antigens have trisaccharide structures [A, GalNAc$\alpha$1-3(Fuc$\alpha$1-2)Gal$\beta$1; and B, Gal$\alpha$1-3(Fuc$\alpha$1-2)Gal$\beta$1] attached to a variety of glycolipids and glycoproteins on the erythrocyte (red blood cell) surface. Group O individuals lack the terminal glycosyltransferases necessary to produce the A or B antigens and carry the disaccharide H antigen (Fuc$\alpha$1-2Gal$\beta$1).

Recent studies suggest that blood group antigen diversity may provide a mechanism of pathogen evasion whereby distinct ABO(H) antigen structures may reduce pathogen attachment and therefore infectivity. Because ABO(H) antigens are composed of carbohydrate structures that only differ by distinct monosaccharides on the terminal structures of glycans, factors that might be responsible for providing innate immunity toward pathogens expressing blood group antigens should recognize carbohydrates.

Bacteria generate a wide variety of glycan-based antigenic structures, many of which can possess blood group antigen activity. For example, *E. coli* O86 cross-reacts with antibodies specific for human blood group B and induces high titers of blood group B-specific antibodies in previously unexposed individuals. Notably, whereas individuals of blood group A or O produce antibodies that kill *E. coli* O86, individuals with blood group B do not generate antibodies capable of altering *E. coli* O86 viability, providing a specific example of the immunological limitation in adaptive immunity toward a blood group antigen-bearing pathogen. Springer & Horton, J. Clin. Invest. 48, 1280-1291 (1969) and see also Vasta, Nat. Rev. Microbiol. 7, 424-438 (2009) entitled "Roles of galectins in infection."

SUMMARY

The disclosure relates to uses of a purified or isolated lectin to kill bacteria, viruses, and other pathogens. In certain embodiments, the disclosure relates to method of treating or preventing an infection comprising administering a purified or isolated lectin to a subject in need thereof. In certain embodiments, the subject is at risk of, exhibiting symptoms of, or diagnosed with a pathogenic infection.

In certain embodiments, the subject is a human subject. In certain embodiments, the lectin is a galectin such as Gal-4, Gal-8, Gal-7, Gal-9 or active fragments thereof provided the galectin comprises a C-terminal carbohydrate recognition domain. Typically, the C-terminal carbohydrate recognition domain or variant thereof is the human C-terminal carbohydrate recognition domain. In certain embodiments, the fragment of Gal-4, Gal-8, and Gal-9 comprises a C-terminal carbohydrate recognition domain. In certain embodiments, the fragment of Gal-9 comprises an N-terminal carbohydrate recognition domain.

In certain embodiments, the disclosure relates to pharmaceutical compositions comprising a galectin such as Gal-4, Gal-8, Gal-7, Gal-9 or fragments thereof. Typically, the galectin comprises a C-terminal carbohydrate recognition domain. In certain embodiments, the disclosure relates to uses of a Gal-4, Gal-8, Gal-7, Gal-9 or fragments thereof provided the galectin comprises a C-terminal carbohydrate recognition domain in the production of a medicament for the treatment or prevention of a pathogenic infection.

In certain embodiments, the subject is diagnosed with blood type B.

In certain embodiments, the pathogen, such as bacteria, virus, or fungus, express a human blood group antigen comprising a carbohydrate on the exterior of the pathogen. Typically, the human blood group antigen is A, B, H, an Rh glycoprotein or combination thereof.

For example, in a particular embodiment, the subject is at risk of, exhibiting symptoms of, or diagnosed with a bacterial infection selected from the group consisting of *Acinetobacter baumannii, Bordetella pertussis, Burkholderia cepacia, Burkholderia pseudomallei, Burkholderia mallei, Campylobacter jejuni, Campylobacter coli, Enterobacter cloacae, Enterobacter aerogenes, Escherichia coli, Francisella tularensis, Haemophilus influenzae, Haemophilus ducreyi, Helicobacter pylori, Klebsiella pneumoniae, Legionella penumophila, Moraxella catarrhalis, Morganella morganii, Neisseria gonorrhoeae, Neisseria meningitidis, Pasteurella multocida, Proteus mirabilis, Proteus vulgaris, Pseudomonas aeruginosa, Salmonella typhi, Serratia marcescens, Shigella flexneri, Shigella boydii, Shigella sonnei, Shigella dysenteriae, Stenotrophomonas maltophilia, Vibrio cholerae,* and *Chlamydia pneumoniae*. In certain embodiments, the bacterium is a gram-negative.

In certain embodiments, the purified or isolated galectin is administered in combination with one or more additional/second antibiotic agents. Typically, the second antibiotic is sulfanilamide, sulfamethizole, sulfamethoxazole, sulfapyridine, trimethoprim, pyrimethamine, nalidixic acids, norfloxacin, ciproflaxin, cinoxacin, dapsone, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam)oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin notrifurantoin, furazolidone, metronidazole, tinidazole, Isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin, polymyxin B, polymyxin B sulfate, procain, spectinomycin, tinidazole, trimethoprim, ramoplanin, teicoplanin, vancomycin, trimethoprim, sulfamethoxazole, and/or nitrofurantoin.

In a specific embodiment, the subject is at risk of, exhibiting symptoms of, or diagnosed with a viral infection such as the influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E, or human immunodeficiency virus (HIV).

In further embodiments, the purified or isolated galectin is administered in combination with one or more of the following antiviral agents: abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

In certain embodiments, the disclosure relates to killing PAO5 expressing bacteria by administering pharmaceutical compositions disclosed herein. In certain embodiments, the disclosure relates to kill bacteria expressing sialylated and terminal lactosamine-containing glycans by administering pharmaceutical compositions disclosed herein.

In certain embodiments, the disclosure relates to pharmaceutical compositions comprising peptides with SEQ ID NO:1, SEQ ID NO:2, SEQ ID NO:3, and/or SEQ ID NO:4. In certain embodiments, the pharmaceutical composition comprises a N-terminal fragment of less than 50, 40, 30, 20, or 10 amino acids as provided for in SEQ ID NO:1, SEQ ID NO:2, SEQ ID NO:3, and/or SEQ ID NO:4. In certain embodiments, the pharmaceutical composition comprises a C-terminal fragment of less than 50, 40, 30, 20, or 10 amino acids as provided for in SEQ ID NO:1, SEQ ID NO:2, SEQ ID NO:3, and/or SEQ ID NO:4,

DETAILED DISCUSSION

Figure 1A:
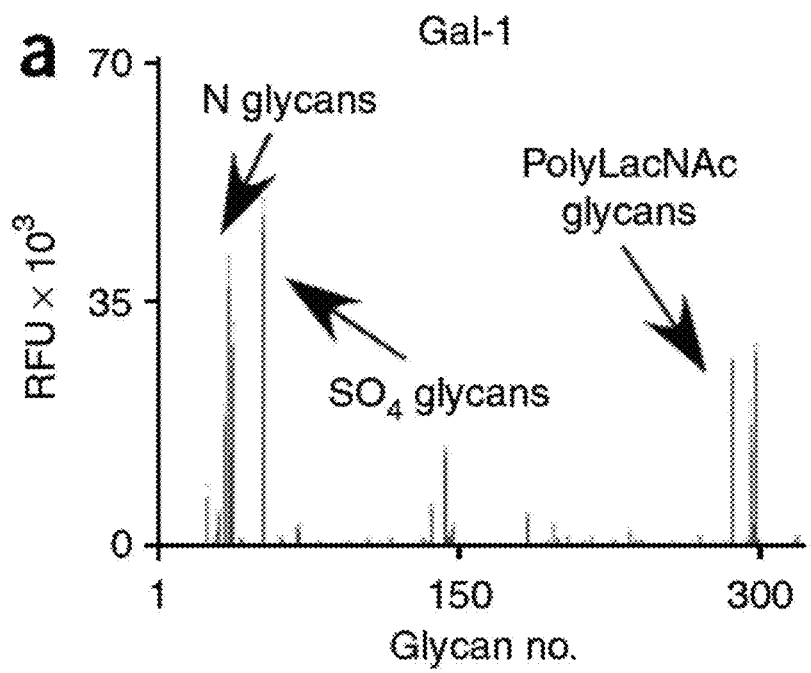
FIG. 1A shows glycan microarray data obtained after incubation with 0.2 µM Gal-1. RFU, relative fluorescence units. Error bars represent means±s.e.m.
Figure 1B:
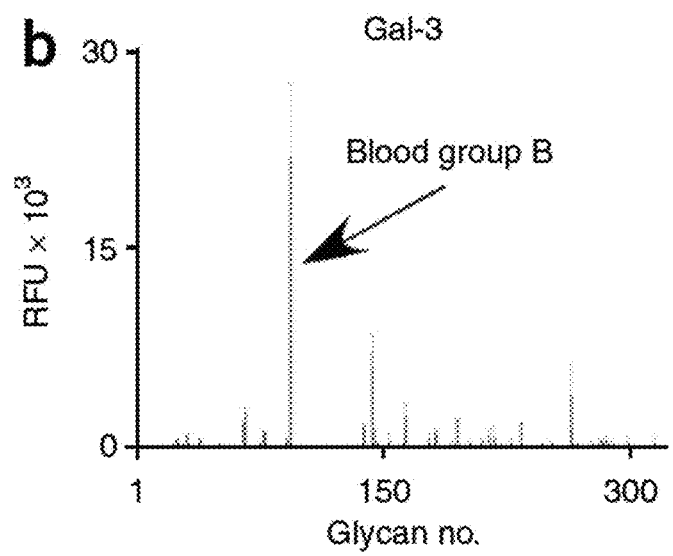
FIG. 1B shows glycan microarray data obtained after incubation with 0.2 µM Gal-3. RFU, relative fluorescence units. Error bars represent means±s.e.m.
Figure 1C:
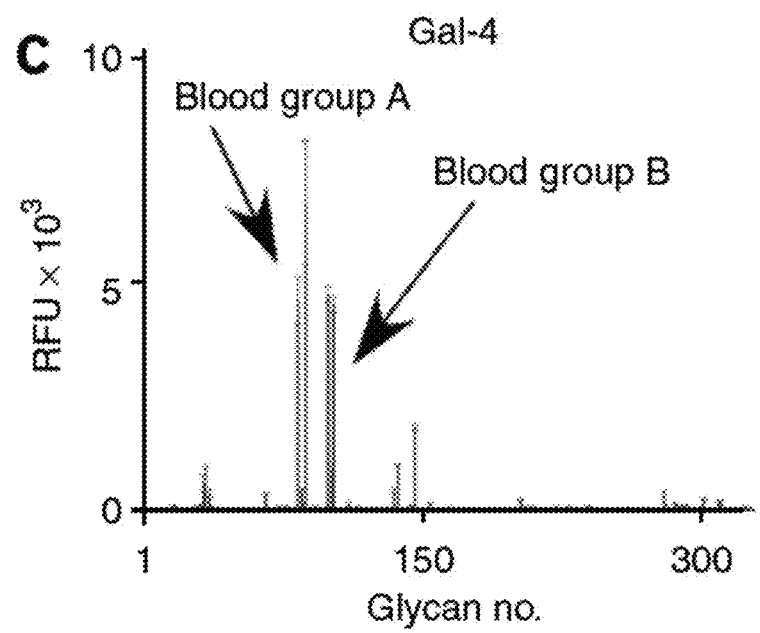
FIG. 1C shows glycan microarray data obtained after incubation with 0.5 µM Gal-4. RFU, relative fluorescence units. Error bars represent means±s.e.m.
Figure 1D:
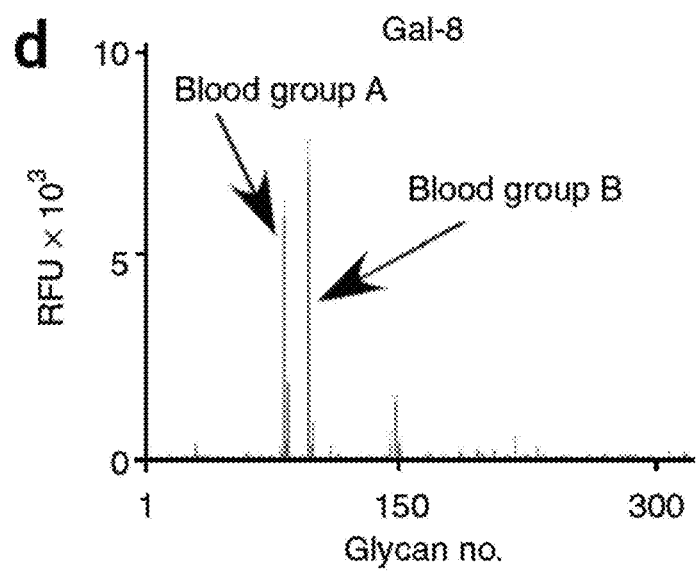
FIG. 1D shows glycan microarray data obtained after incubation with 0.02 µM Gal-8. RFU, relative fluorescence units. Error bars represent means±s.e.m.

It has been discovered that certain innate immune lectins, e.g., galectin-4 (Gal-4), galectin-7 (Gal-7), galectin-8 (Gal-8) and, galectin Gal-9 (Gal-9) recognize and kill pathogens. The killing activity of Gal-4 and Gal-8 is mediated by their C-terminal domains, occurs rapidly and independently of complement and is accompanied by disruption of membrane integrity. These results demonstrate that innate defense lectins can provide immunity against pathogens that express blood group-like antigens on their surface and suggests that pharmaceutical compositions that contain these domains are useful for the treatment or prevention of certain bacterial infections or infection of other pathogens.

Lectins Kill Bacteria Expressing Blood Group Antigen

The expression of ABO(H) blood group antigens causes deletion of cells that generate self-specific antibodies to these antigens but this deletion limits adaptive immunity toward pathogens bearing cognate blood group antigens. To explore potential defense mechanisms against such pathogens, given these limitations in adaptive immunity, innate proteins that could recognize human blood group antigens were screened. Two innate immune lectins, Gal-4 and Gal-8, which are expressed in the intestinal tract, recognize and kill human blood group antigen-expressing *Escherichia coli* while failing to alter the viability of other *E. coli* strains or certain other Gram-negative or Gram-positive organisms both in vitro and in vivo. The killing activity of both Gal-4 and Gal-8 is mediated by their C-terminal domains, occurs rapidly and independently of complement and is accompanied by disruption of membrane integrity. The ability of Gal-4 and Gal-8 to specifically kill BGB$^+$ *E. coli* extends previous observations suggesting roles for galectins in innate immunity and may reflect a common but unrealized feature of other innate immune lectins to provide direct protection against pathogens expressing particular self-like antigens, where adaptive immunity cannot.

Similar to many innate immune factors, the galectins represent proteins present in a wide variety of species. As galectins evolved long before the selection of adaptive immunity, it is intriguing to speculate that the types of carbohydrate modifications on some self-antigens, such as blood group antigens, may reflect the binding specificity of preexisting innate immune factors such as the galectins. The generation of ABO(H) antigen diversity in the human population has been proposed to facilitate pathogen evasion during human evolution. See Rowe et al. Proc. Natl. Acad. Sci. USA 104, 17471-17476 (2007). For example, differential expression of blood group ABO(H) antigens in host tissues can differentially affect pathogen adhesion and infection. However, this diversity might have arisen with a considerable fitness cost, as development of these antigens precludes adaptive immune responses against blood group antigen-bearing pathogens. The ability of galectins to recognize blood group antigen-bearing pathogens may have facilitated the selection of ABO(H) expression on human erythrocytes rather than alternative antigens that did not have the same preexisting innate immune protection. In contrast, the ability of Gal-4 and Gal-8 to also kill α-Gal-expressing bacteria shows that galectin-mediated killing is not limited to human blood group antigen-expressing bacteria and suggests that galectins may affect the composition of multiple populations of intestinal bacteria, thereby modulating the intestinal microbiome.

Pharmaceutical Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid, and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g., NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include: the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of methods of structuring a compound as prodrugs can be found in the book of Testa and Mayer, Hydrolysis in Drug and Prodrug Metabolism, Wiley (2006), which is incorporated herein by reference. Typical prodrugs form the active metabolite by transformation of the prodrug by hydrolytic enzymes, the hydrolysis of amide, lactams, peptides, carboxylic acid esters, epoxides or the cleavage of esters or inorganic acids.

Pharmaceutical compositions typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087, and U.S. Pat. No. 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087, and U.S. Pat. No. 6,372,733 and the further references mentioned above, as well as to the standard handbooks, such as the latest edition of Remington's Pharmaceutical Sciences.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein, "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers, and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid, and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions that include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine, and lauryl sulfobetaine.

If desired, the tablets, beads, granules, or particles may also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma sold as Eudragit®. In further preferred embodiments, the acrylic polymer comprises a mixture of two acrylic resin lacquers commercially available from Rohm Pharma sold as Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above, such as Eudragit® RL/RS, may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours, and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose, and waxes can also serve as binders. A lubricant is necessary in a tablet formulation to prevent the tablet and punches from sticking in the die. The lubricant is chosen from such slippery solids as talc, magnesium and calcium stearate, stearic acid, and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein; and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil, and acetylated monoglycerides. A stabilizing agent is preferably used to stabilize particles in the dispersion. Typical stabilizing agents are nonionic emulsifiers such as sorbitan esters, polysorbates, and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants, such as magnesium stearate and glycerol monostearates, may also be used. Pigments, such as titanium dioxide, may also be used. Small quantities of an antifoaming agent, such as a silicone (e.g., simethicone), may also be added to the coating composition.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

TERMS

A "lectin" refers to a carbohydrate binding protein, e.g., but not limited to, mannose, glactose, glucosamine, and fructose binding lectins. The galectins are lectins that are beta-galactoside-binding proteins, such as lactose, implicated in modulating cell-cell and cell-matrix interactions. The expression of galectins is thought to be is restricted to small intestine, colon, and rectum.

Galectin-4 (Gal-4) has SEQ ID NO 1:

MAYVPAPGYQPTYNPTLPYYQPIPGGLNVGMSVYIQGVASEHM

KRFFVNFVVGQDPGSDVAFHFNPRFDGWDKVVFNTLQGGKWGS

EERKRSMPFKKGAAFELVFIVLAEHYKVVVNGNPFYEYGHRLP

LQMVTHLQVDGDLQLQSINFIGGQPLRPQGPPMMPPYPGPGHC

HQQLNSLPTMEGPPTFNPPVPYFGRLQGGLTARRTIIIKGYVP

PTGKSFAINFKVGSSGDIALHINPRMGNGTVVRNSLLNGSWGS

EEKKITHNPFGPGQFFDLSIRCGLDRFKVYANGQHLFDFAHRL

SAFQRVDTLEIQGDVTLSYVQi

Galectin-7 (Gal-7) has SEQ ID NO 2:

MSNVPHKSSLPEGIRPGTVLRIRGLVPPNASRFHVNLLCGEEQ

GSDAALHFNPRLDTSEVVFNSKEQGSWGREERGPGVPFQRGQP

FEVLIIASDDGFKAVVGDAQYHHFRHRLPLARVRLVEVGGDVQ

LDSVRIF

Galectin-8 (Gal-8) has SEQ ID NO 3:

MMLSLNNLQNIIYNPVIPFVGTIPDQLDPGTLIVIRGHVPSDA

DRFQVDLQNGSSMKPRADVAFHFNPRFKRAGCIVCNTLINEKW

GREEITYDTPFKREKSFEIVIMVLKDKFQVAVNGKHTLLYGHR

IGPEKIDTLGIYGKVNIHSIGFSFSSDLQSTQASSLELTEISR

ENVPKSGTPQLPSNRGGDISKIAPRTVYTKSKDSTVNHTLTCT

KIPPMNYVSKRLPFAARLNTPMGPGRTVVVKGEVNANAKSFNV

DLLAGKSKDIALHLNPRLNIKAFVRNSFLQESWGEEERNITSF

PFSPGMYFEMIIYCDVREFKVAVNGVHSLEYKHRFKELSSIDT

LEINGDIHLLEVRSW

Galectin-9 (Gal-9) has SEQ ID NO 4

MAFSGSQAPYLSPAVPFSGTIQGGLQDGLQITVNGTVLSSSGT

RFAVNFQTGFSGNDIAFHFNPRFEDGGYVVCNTRQNGSWGPEE

RKTHMPFQKGMPFDLCFLVQSSDFKVMVNGILFVQYFHRVPFH

RVDTISVNGSVQLSYISFQPPGVWPANPAPITQTVIHTVQSAP

GQMFSTPAIPPMMYPHPAYPMPFITTILGGLYPSKSILLSGTV

LPSAQRFHINLCSGNHIAFHLNPRFDENAVVRNTQIDNSWGSE

ERSLPRKMPFVRGQSFSVWILCEAHCLKVAVDGQHLFEYYHRL

RNLPTINRLEVGGDIQLTHVQT

The terms "Gal-4," "Gal-7," "Gal-8," "Gal-9" and N- and C-terminal binding domains are not necessarily intended to be limited to the specific sequences provided above. Minor changes and derivatization may result in a molecule that continues to bind beta-galactoside, and it is intended that the term include such isoforms, homologs, analogs, variants, fragments or derivatives thereof. For example, the Gal-8 gene is relatively conserved in chimpanzee, dog, cow, mouse, rat, chicken, and zebrafish, and the term is intended to include these homologs, isoforms, analogs, variants, fragments or derivatives thereof.

Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups: glycine for alanine; valine for isoleucine or for leucine; aspartic acid for glutamic acid; asparagine for glutamine; serine for threonine; lysine for arginine; phenylalanine for tyrosine; and vice versa.

Modifications (which do not normally alter primary sequence) include in vivo or in vitro chemical derivatization of polypeptides, e.g., acetylation, or carboxylation. Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the disclosure are not limited to products of any of the specific exemplary processes listed herein.

In certain embodiments, the present disclosure should also be construed to encompass "mutants," "derivatives," and "variants" of the peptides disclosed herein (or of the DNA encoding the same) which are altered in one or more amino acids (or, when referring to the nucleotide sequence encoding the same, are altered in one or more base pairs) such that the resulting peptide (or DNA) is not identical to the sequences recited herein, As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "salts" refer to derivatives of the disclosed compounds where the parent compound is modified making acid or base salts thereof. Examples of salts include, but are not limited to, mineral or organic acid salts of basic residues, such as amines, alkylamines, or dialkylamines; alkali or organic salts of acidic residues such as carboxylic acids; and the like. In the preferred embodiments, the salts are conventional nontoxic pharmaceutically acceptable salts including the quaternary ammonium salts of the parent compound formed, and non-toxic inorganic or organic acids. Preferred salts include those derived from inorganic acids, such as hydrochloric, hydrobromic, sulfuric, sulfamic, phosphoric, nitric, and the like; and the salts prepared from organic acids, such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

EXPERIMENTAL

Example 1

Galectins Recognize Blood Group-Positive Bacteria

Publicly available data from the screening of nearly 100 different lectins from the Consortium for Functional Glycomics, many of which are mammalian lectins with documented immunological activity, including members of the galectin family was analyzed. Members of the galectin family had some of the most specific interactions observed among the lectins tested after screening of over 300 structurally diverse glycans. Human Gal-3, Gal-4 and Gal-8, which recognize multiple glycan structures at relatively high concentrations showed specificity for human blood group A and B antigens at submicromolar concentrations and did not bind blood group O(H) at these concentrations, whereas human Gal-1, a related galectin family member, did not recognize blood group antigens (FIG. 1a-d). This specificity was not as striking in previous studies concerning members of this protein family, where binding at high protein concentrations was tested. The lectins were found to recognized multiple carbohydrate ligands along with blood group antigens. Stowell et al., J. Biol. Chem. 283, 10109-10123 (2008). Stowell et al., J. Biol. Chem. 283, 20547-20559 (2008).

Figure 1E:
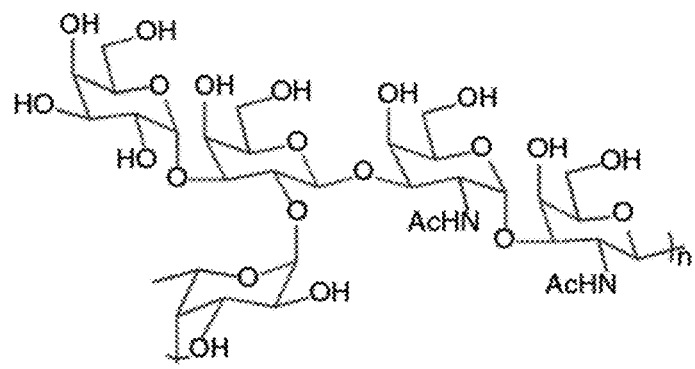
FIG. 1E illustrates the structure of *E. coli* O86 O antigen.
Figure 1F:
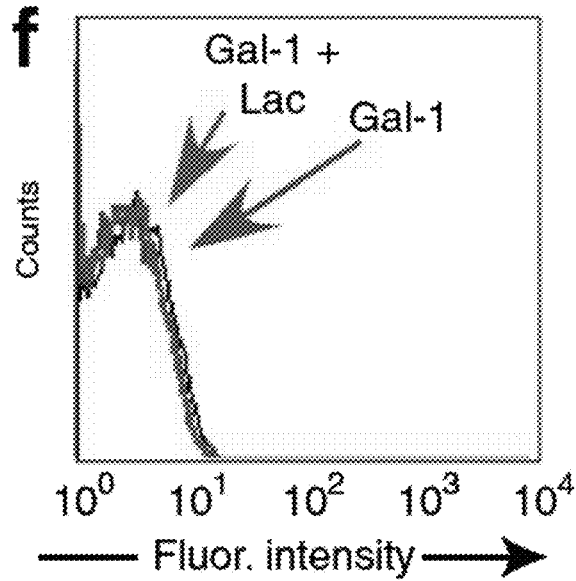
FIG. 1F shows flow cytometric analysis of BGB$^+$ *E. coli* counts after incubation of BGB$^+$ *E. coli* with Gal-1 tested at ~0.1 µM with or without inclusion of 20 mM lactose (Lac) where indicated.
Figure 1G:
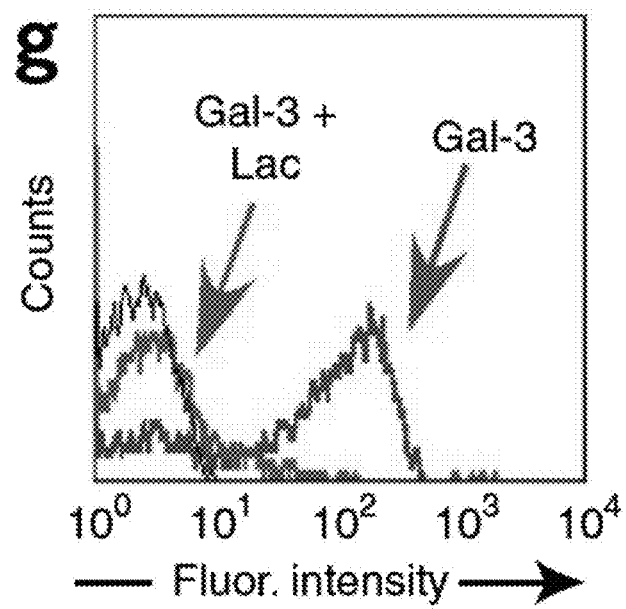
FIG. 1G shows flow cytometric analysis of BGB$^+$ *E. coli* counts after incubation of BGB$^+$ *E. coli* with Gal-3 tested at ~0.1 µM with or without inclusion of 20 mM lactose (Lac) where indicated.
Figure 1H:
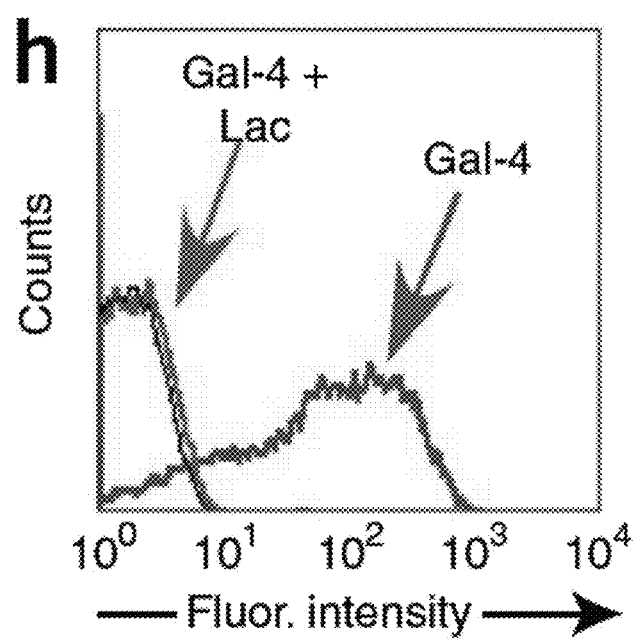
FIG. 1H shows flow cytometric analysis of BGB$^+$ *E. coli* counts after incubation of BGB$^+$ *E. coli* with Gal-4 tested at ~0.1 µM with or without inclusion of 20 mM lactose (Lac) where indicated.
Figure 1I:
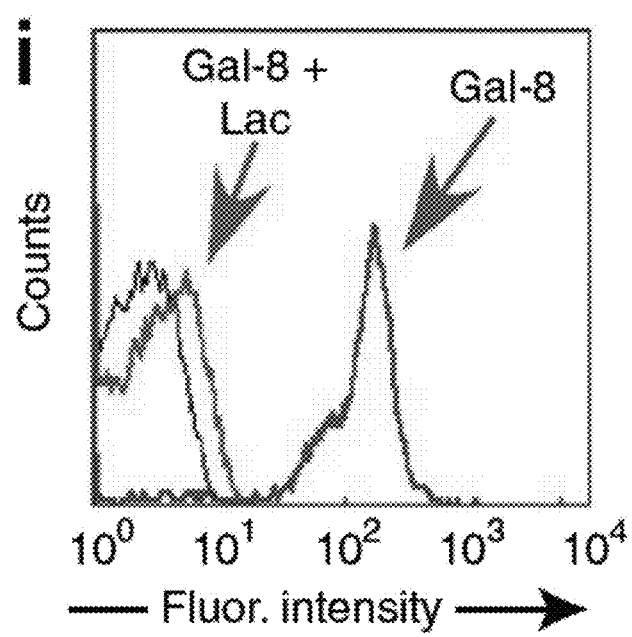
FIG. 1I shows flow cytometric analysis of BGB$^+$ *E. coli* counts after incubation of BGB$^+$ *E. coli* with Gal-8 tested at ~0.1 µM with or without inclusion of 20 mM lactose (Lac) where indicated.

Bacteria generate a wide variety of glycan-based antigenic structures, many of which can possess blood group antigen activity. *E. coli* O86, cross-reacts with antibodies specific for human blood group B and induces high titers of blood group B-specific antibodies in previously unexposed individuals. Notably, whereas individuals of blood group A or O produce antibodies that kill *E. coli* O86, individuals with blood group B do not generate antibodies capable of altering *E. coli* O86 viability, providing a specific example of the immunological limitation in adaptive immunity toward a blood group antigen-bearing pathogen. Although *E. coli* O86 generates an identical blood group B epitope (FIG. 1e) to that of humans, the context of this epitope may differ from the common human presentations found on the glycan microarray. Therefore, whether Gal-3, Gal-4 and Gal-8 recognize *E. coli* O86 was examined. Consistent with their ability to specifically recognize blood group A and B antigens on the glycan microarray, human Gal-3, Gal-4 and Gal-8, but not Gal-1, bound *E. coli* O86, hereafter referred to as blood group B-positive *E. coli* ($BGB^+$ *E. coli*) (FIG. 1f-i). Binding of all galectins to bacteria was inhibited by lactose, an inhibitor of galectin-carbohydrate interactions (FIG. 1f-i), indicating that galectin bound glycan determinants on the surface of $BGB^+$ *E. coli*.

Example 2

Gal-4 and Gal-8 Kill Blood Group-Positive Bacteria

Studies showed high galectin expression in the intestinal mucosa, where the galectins may serve as pathogen recognition proteins, suggesting that Gal-3, Gal-4 and Gal-8 may facilitate innate immunity toward $BGB^+$ pathogens. Although studies disclose that several innate immune lectins can directly affect pathogen viability, there is no direct evidence as to whether galectins can alter prokaryote viability. See Cash et al., Science 313, 1126-1130 (2006), Vasta, Nat. Rev. Microbiol. 7, 424-438 (2009), Kohatsu et al. J. Immunol. 177, 4718-4726 (2006), and Thiel, S. et al. Nature 386, 506-510 (1997).

Figure 2A:
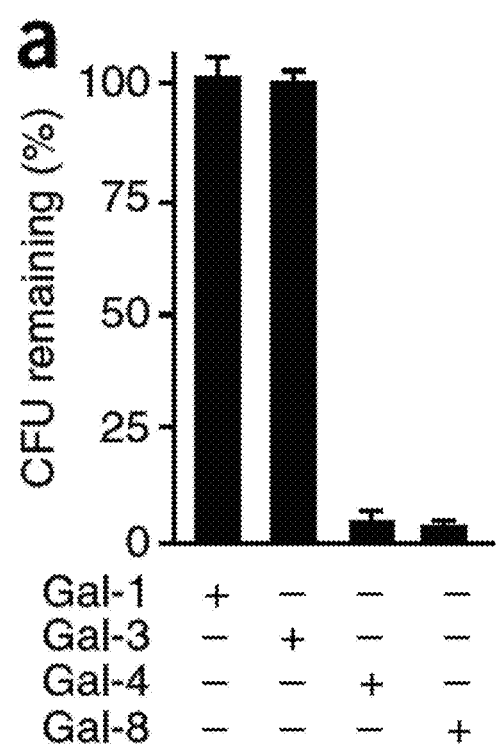
FIG. 2A shows data on the quantification of viable bacteria after BGB$^+$ *E. coli* were mixed with 5 µM Gal-1, Gal-3, Gal-4 or Gal-8. In each experiment, bacteria were quantified by dilution plating, n=3; one representative experiment in duplicate over two dilutions is shown.
Figure 2B:
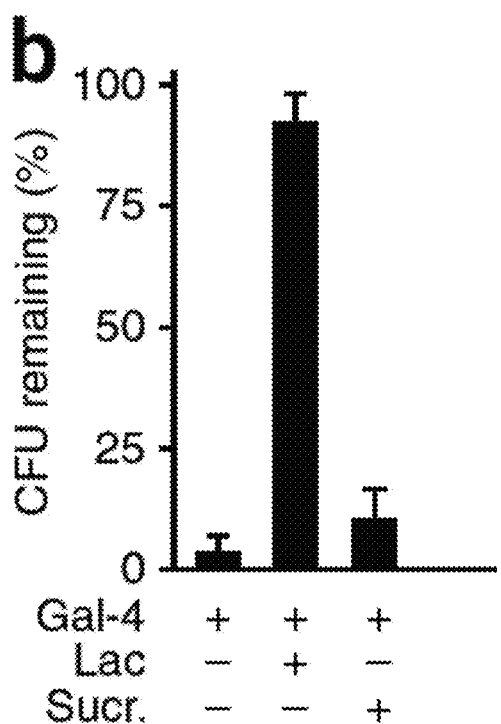
FIG. 2B show data on the quantification of viable bacteria after BGB$^+$ *E. coli* were mixed with 5 µM Gal-4 with or without 20 mM lactose (Lac) or 20 mM sucrose (Sucr.).
Figure 2C:
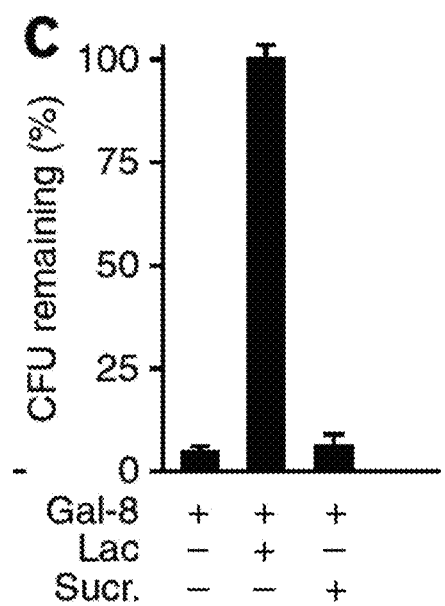
FIG. 2C shows data on the quantification of viable bacteria after BGB$^+$ *E. coli* were mixed with 5 µM Gal-8 with or without 20 mM lactose (Lac) or 20 mM sucrose (Sucr.).
Figure 2D:
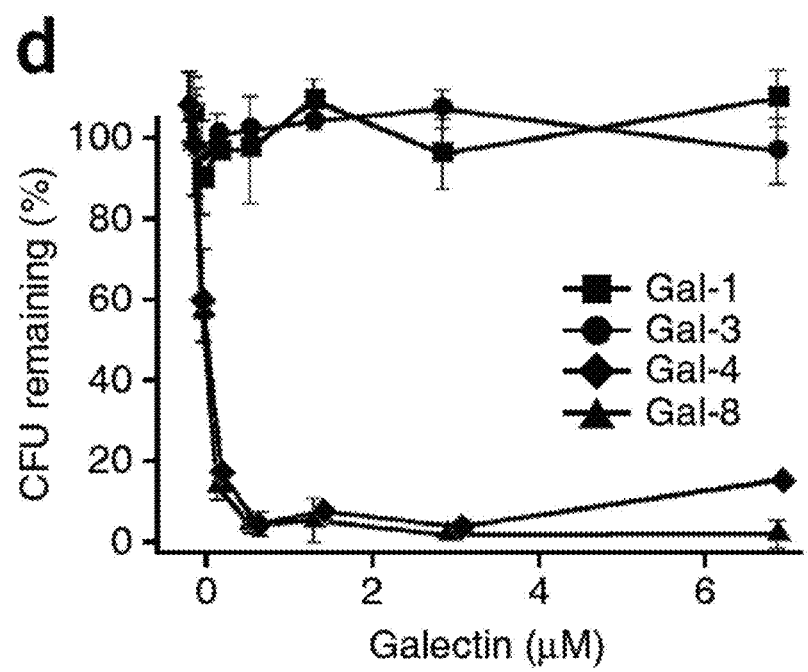
FIG. 2D shows data on the quantification of viable bacteria after BGB$^+$ *E. coli* were mixed with the indicated concentrations of Gal-1, Gal-3, Gal-4 and Gal-8.
Figure 2E:
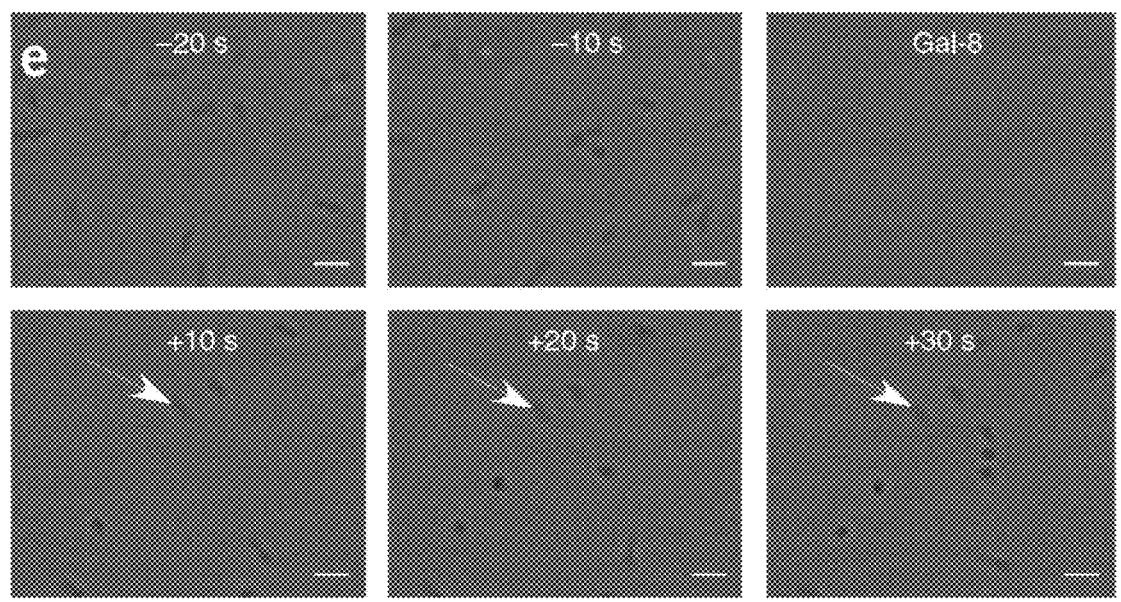
FIG. 2E shows still-frame images from real-time video microscopy showing bacterial mobility at 10-s intervals before and after addition of 5 µM Gal-8, as indicated. Arrows indicate one group of immobilized bacteria. Scale bars, 100 µm.
Figure 2F:
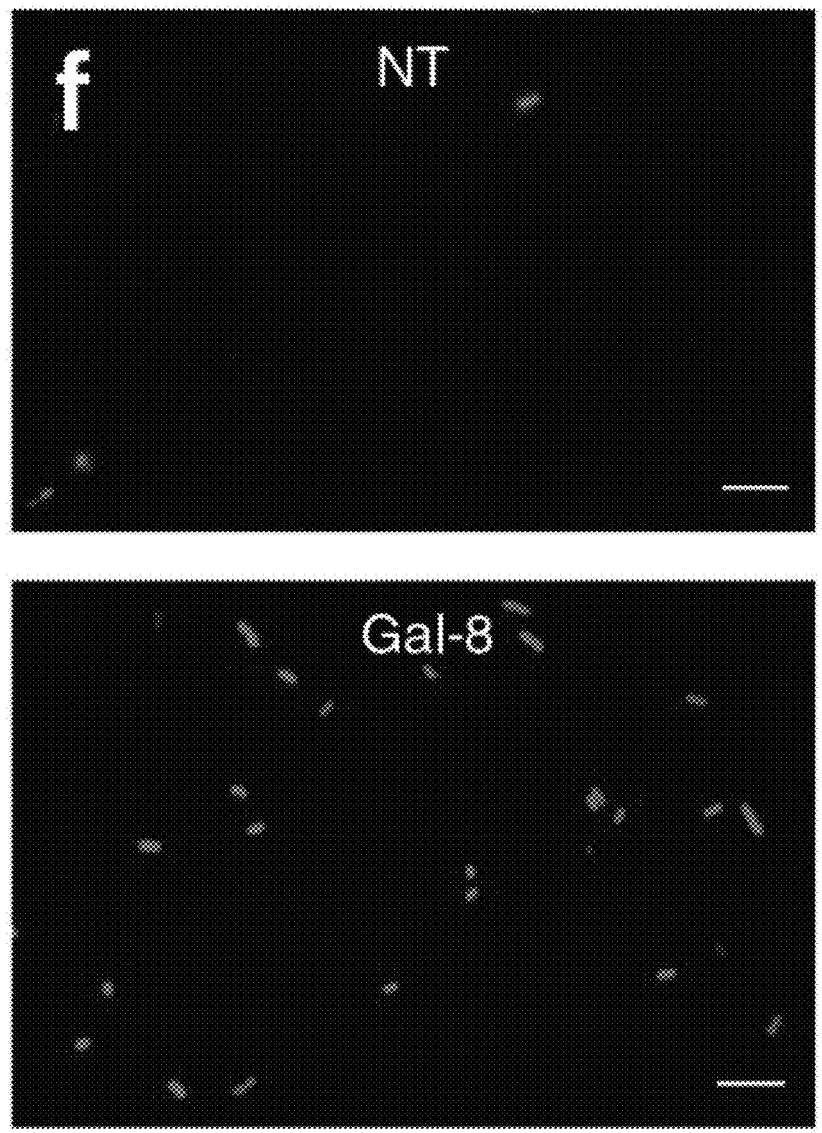
FIG. 2F shows fluorescence microscopy images of BGB$^+$ *E. coli* grown to mid-log phase followed by addition of 5 µM Gal-8. Untreated and Gal-8-treated bacteria were stained with propidium iodide (red). Scale bars, 100 µm.
Figure 2G:
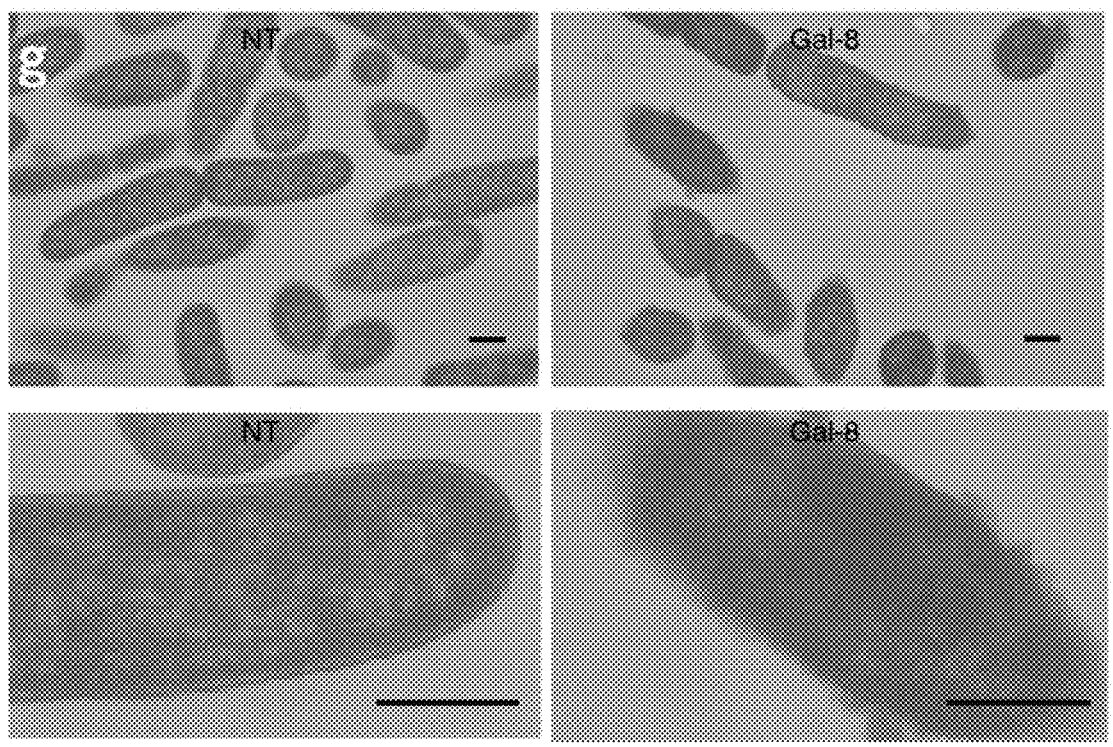
FIG. 2G shows transmission electron microscopy images of BGB+ *E. coli* after addition of PBS (NT) or 5 μM Gal-8. The bottom images show an enlarged view of a single bacterium. Scale bars, 500 nm.
Figure 2H:
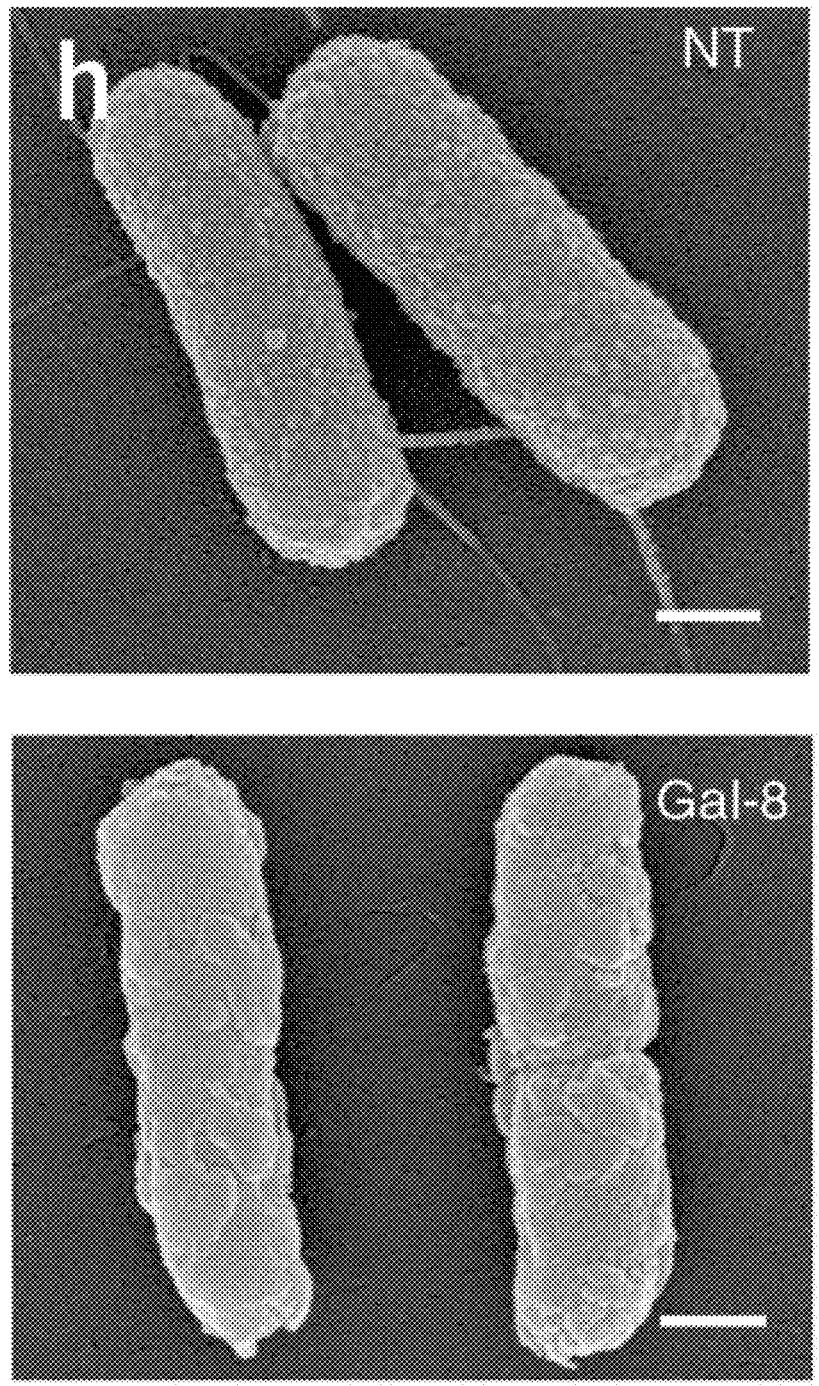
FIG. 2H shows scanning electron microscopy images of BGB+ *E. coli* followed by addition of PBS (NT) or Gal-8. Scale bars, 500 nm.

Whether galectins might confer intrinsic immunity by directly killing $BGB^+$ *E. coli* was examined. Incubation with both Gal-4 and Gal-8 caused direct killing of $BGB^+$ *E. coli*, whereas Gal-3, which also binds $BGB^+$ *E. coli*, did not affect viability, and Gal-1, which does not bind $BGB^+$ *E. coli*, had no effect (FIG. 2a). Lactose completely inhibited both Gal-4- and Gal-8-induced death, whereas sucrose, a disaccharide unable to inhibit galectin-carbohydrate interactions, failed to alter killing of $BGB^+$ *E. coli* (FIG. 2b,c). Gal-4 and Gal-8 showed similarly potent concentration-dependent killing of $BGB^+$ *E. coli*, with a half-maximal lethal dose of ~0.1 µM (FIG. 2d), a concentration similar to that observed in vivo and used to evaluate glycan binding specificity on the glycan microarray. In addition, the effects of Gal-8 treatment seemed to be rapid, as treated $BGB^+$ *E. coli* lost all motility compared to untreated $BGB^+$ *E. coli* shortly after the addition of Gal-8 (FIG. 2e). $BGB^+$ *E. coli* positively stained for propidium iodide after a 30 min incubation with Gal-8 (FIG. 2f) and showed considerable disruption of membrane morphology (FIG. 2g,h). These results show that Gal-8 kills $BGB^+$ *E. coli* by directly altering membrane integrity. Comparable alterations were observed after incubation with Gal-4 (data not shown). Taken together, these results show that both human Gal-4 and Gal-8 directly kill $BGB^+$*E. coli* through recognition of bacterial surface carbohydrates via a mechanism that drastically alters membrane integrity and bacterial motility. Killing of $BGB^+$ *E. coli* by human Gal-4 and Gal-8 did not require complement (FIG. 2), demonstrating that these lectins fundamentally differ from other innate immune lectins, such as mannan-binding proteins, which do not directly alter viability but activate complement after pathogen recognition.

Figure 3A:
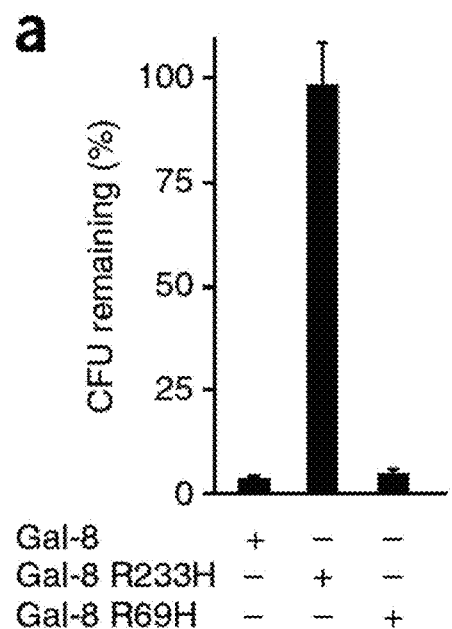
FIG. 3A shows data on the quantification of BGB+ *E. coli* after addition of 5 μM Gal-8, Gal-8R233H or Gal-8R69H at mid-log phase. Viable bacteria were quantified by dilution plating, n=3 experiments; one representative experiment in duplicate over two dilutions is shown; error bars represent means±s.d. of duplicates.
Figure 3B:
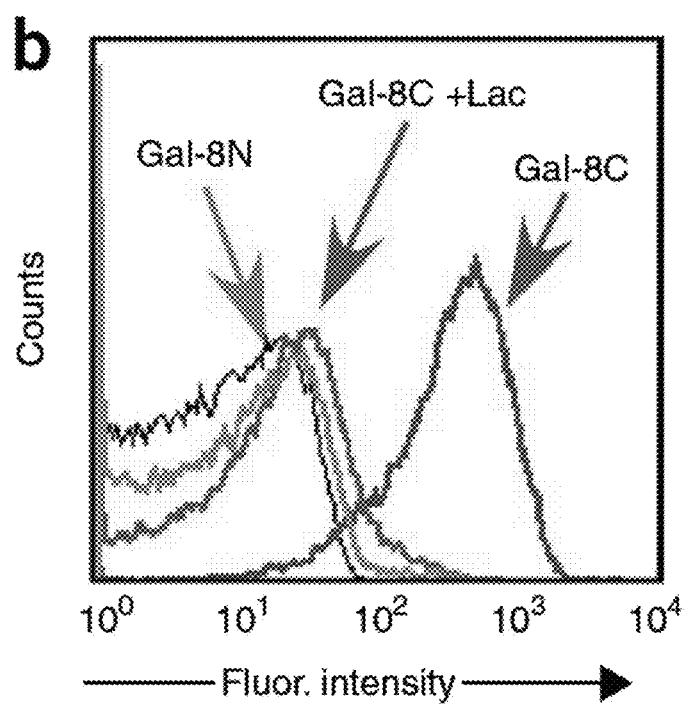
FIG. 3B shows flow cytometric analysis of BGB+ *E. coli* counts after incubation of BGB+ *E. coli* with Gal-8N or Gal-8C at ~0.1 μM with or without inclusion of 20 mM lactose (Lac) where indicated.
Figure 3C:
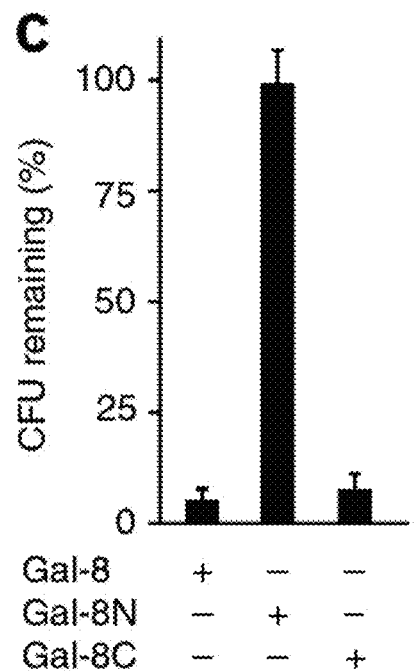
FIG. 3C shows data on the quantification of BGB+ *E. coli* after addition of 5 μM Gal-8, Gal-8N or Gal-8C at mid-log phase. Viable bacteria were quantified by dilution plating, n=3 experiments; one representative experiment in duplicate over two dilutions shown; error bars represent means±s.d. of duplicates.
Figure 3D:
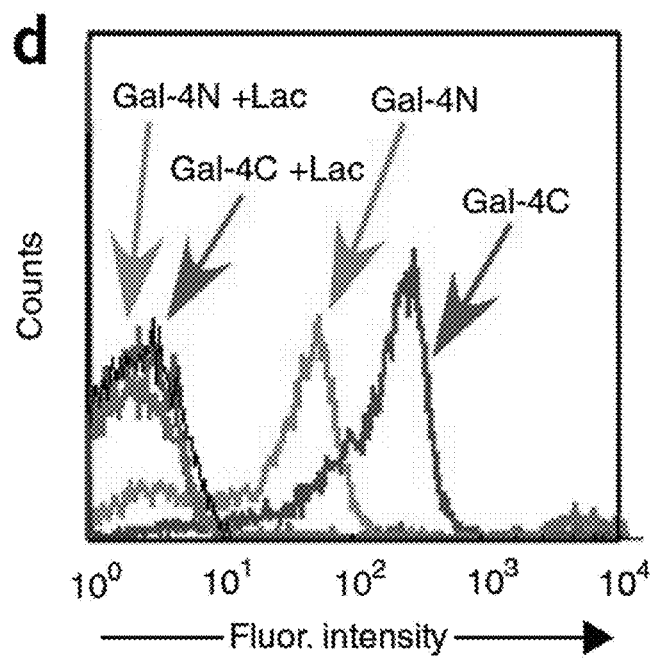
FIG. 3D shows flow cytometric analysis of BGB+ *E. coli* counts after incubation of BGB+ *E. coli* with Gal-4N or Gal-4C at ~0.1 μM with or without inclusion of 20 mM lactose (Lac) where indicated.
Figure 3E:
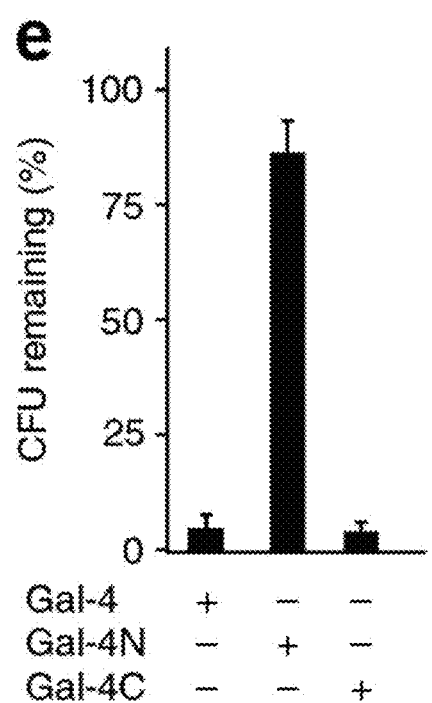
FIG. 3E shows data on the quantification of BGB+ *E. coli* after addition of 5 μM Gal-4, Gal-4N or Gal-4C at mid-log phase. Viable bacteria were quantified by dilution plating; n=3 experiments; one representative experiment in duplicate over two dilutions shown; error bars represent means±s.d. of duplicates.

Unlike Gal-1 and Gal-3, which contain a single carbohydrate recognition domain (CRD), Gal-4 and Gal-8 have two distinct CRDs, suggesting that these galectins may use one domain for target recognition and the other domain for killing the target once bound, similarly to many prokaryotic AB toxins. To distinguish these possibilities, we mutated each CRD of Gal-8, in the context of the whole protein, to determine which domain recognizes $BGB^+$ *E. coli*. Inactivation of the C-terminal CRD (R233H) (Gal-8R233H) eliminated recognition of blood group antigens on both the glycan microarray and $BGB^+$ *E. coli*, whereas the analogous mutation in the N-terminal CRD (R69H) (Gal-8R69H) did not alter blood group antigen recognition in either context. Of note, Gal-8R69H, but not Gal-8R233H, killed $BGB^+$ *E. coli* (FIG. 3a), which indicates that Gal-8-mediated killing requires carbohydrate recognition only by the blood group-binding C-terminal domain of Gal-8. To determine whether the N-terminal domain is required for Gal-8 killing independently of glycan recognition, the individual domains of Gal-8 were expressed. Whereas the N-terminal domain (Gal-8N) failed to bind blood group antigens on either the glycan microarray or $BGB^+$ *E. coli* (FIG. 3b and data not shown), the C-terminal domain of Gal-8 (Gal-8C) independently recognized blood group antigens and killed $BGB^+$ *E. coli* (FIG. 3b,c). These results show that recognition and killing of $BGB^+$ *E. coli* by Gal-8 resides entirely within its blood group-binding domain. By contrast, both domains of Gal-4 showed specific recognition of $BGB^+$ *E. coli* (FIG. 3d). Thus, we asked whether Gal-4N and Gal-4C might independently kill $BGB^+$ *E. coli*. However, similar to Gal-3, Gal-4N showed substantial recognition of $BGB^+$ *E. coli* yet failed to alter $BGB^+$ *E. coli* viability (FIG. 2a and FIG. 3e). By contrast, Gal-4C had substantial killing activity toward $BGB^+$ *E. coli* (FIG. 3e). Notably, the Gal-4C and Gal-8C domains show phylogenetic similarities not shared by Gal-3 and the Gal-4N domain, which suggests a conserved mechanism shared between these two protein domains.

Example 3

Galectin Killing Requires Blood Group Antigen Recognition

Figure 4A:
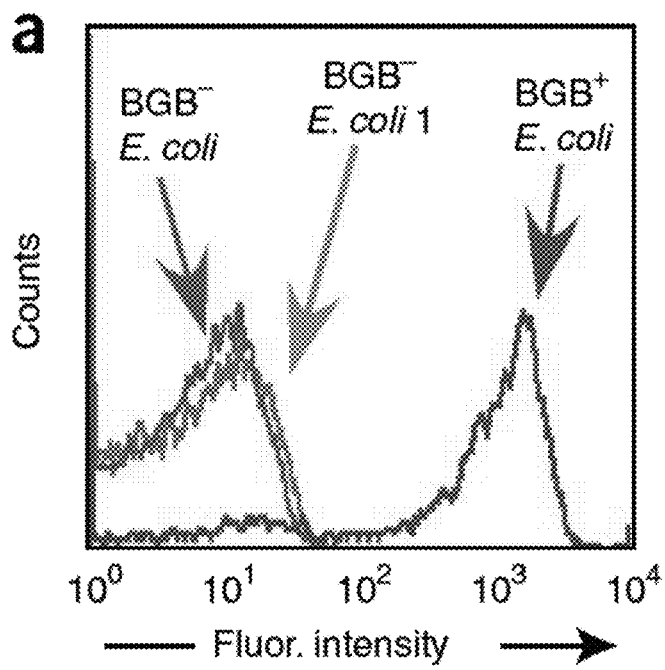
FIG. 4A shows flow cytometric analysis of galectin binding after incubation of BGB+*E. coli* and two different BGB− *E. coli* reference strains obtained from a clinical laboratory with ~0.1 μM Gal-8.
Figure 4B:
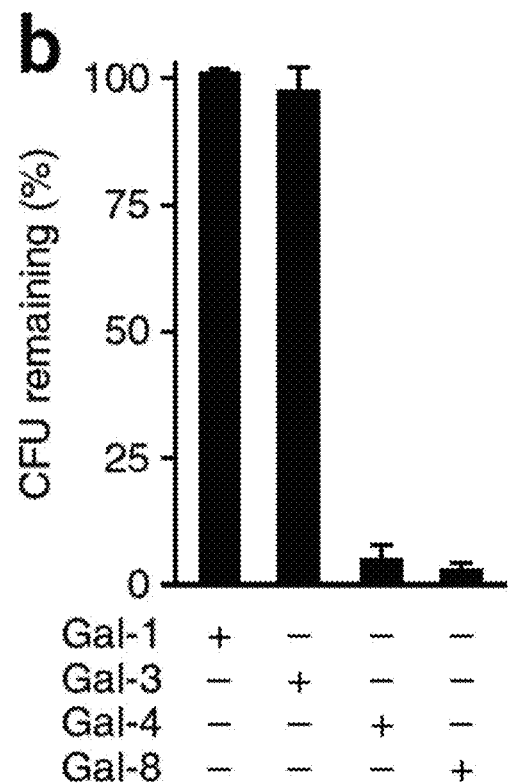
FIG. 4B shows data on the quantification of BGB+ *E. coli* after incubation with 5 μM Gal-1, Gal-3, Gal-4 or Gal-8, as indicated. Viable bacteria were quantified by dilution plating; n=3 experiments; one representative experiment in duplicate over two dilutions is shown; error bars represent means±s.d.
Figure 4C:
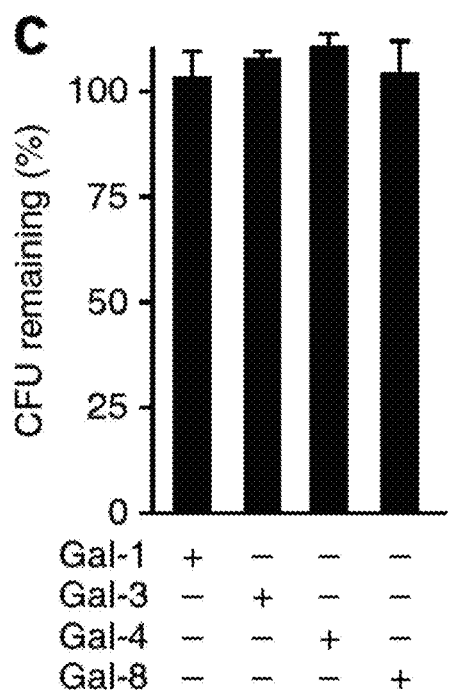
FIG. 4C shows data on the quantification of BGB− *E. coli* strain 1 after incubation with 5 μM Gal-1, Gal-3, Gal-4 or Gal-8, as indicated. Viable bacteria were quantified by dilution plating; n=3 experiments; one representative experiment in duplicate over two dilutions is shown; error bars represent means±s.d.
Figure 4D:
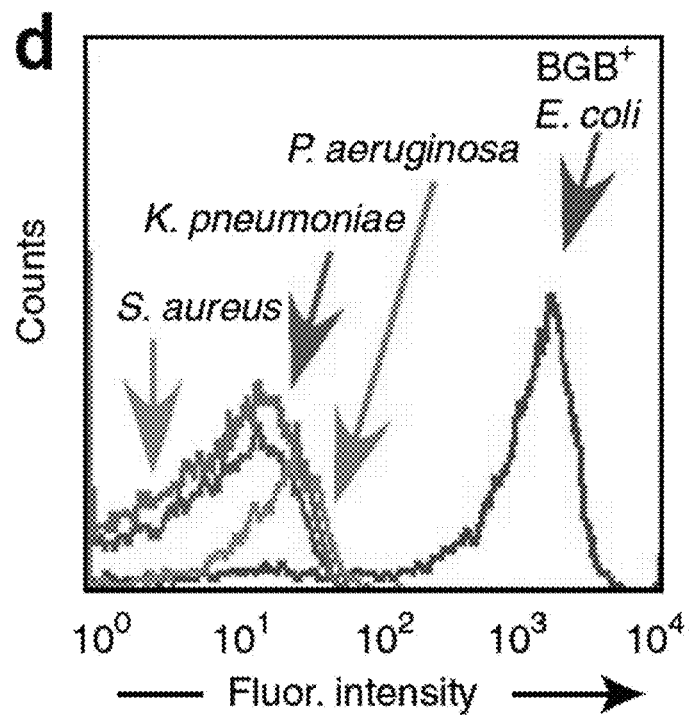
FIG. 4D shows flow cytometric analysis of galectin binding after incubation of BGB+*E. coli*, *K. pneumoniae*, *P. aeruginosa* or *S. aureus* with ~0.1 μM Gal-8.
Figure 4E:
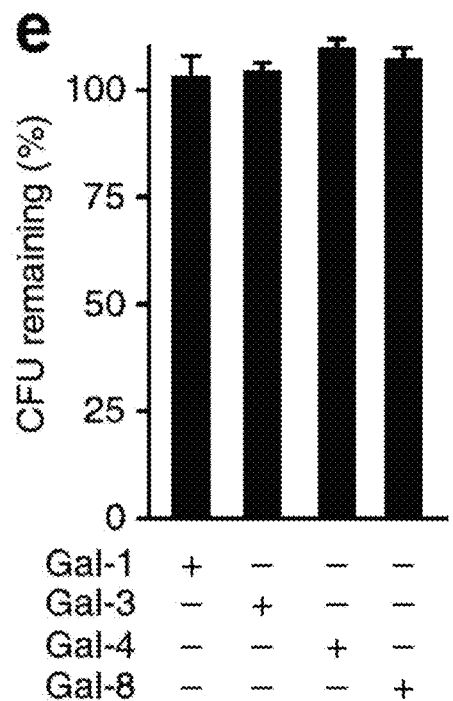
FIG. 4E shows data on the quantification of *K. pneumoniae* with 5 μM Gal-1, Gal-3, Gal-4 or Gal-8, as indicated. Viable bacteria were quantified by dilution plating; n=3 experiments; one representative experiment in duplicate over two dilutions is shown; error bars represent means±s.d.
Figure 4F:
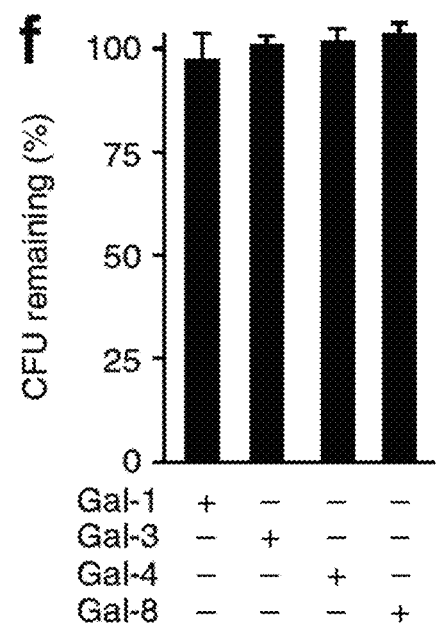
FIG. 4F shows data on the quantification of *P. aeruginosa* with 5 μM Gal-1, Gal-3, Gal-4 or Gal-8, as indicated.
Figure 4G:
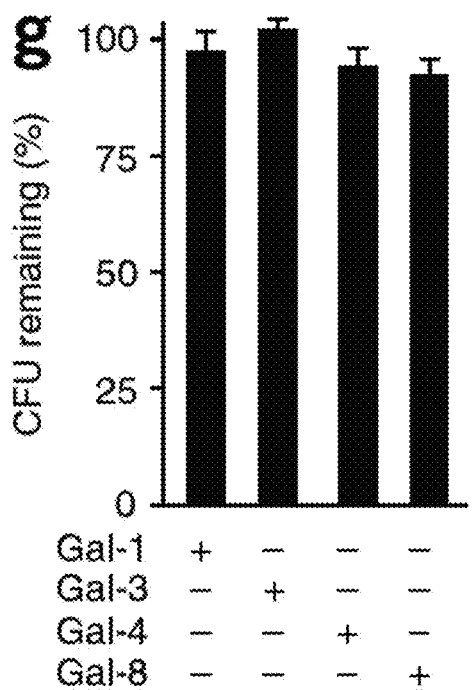
FIG. 4G shows data on the quantification of *S. aureus* with 5 μM Gal-1, Gal-3, Gal-4 or Gal-8, as indicated.
Figure 4H:
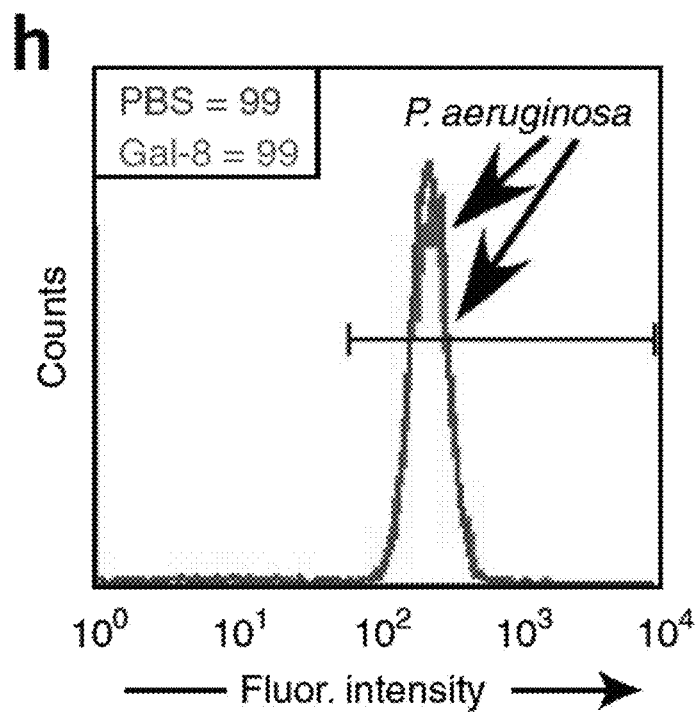
FIG. 4H shows data on the quantification of GFP+ *P. aeruginosa* alone (h) after incubation with or without 5 μM Gal-8 followed by determination of percentage GFP+ *P. aeruginosa* by flow cytometric analysis in a mixing experiment. Gated counts of GFP+ bacteria treated with PBS (blue) or Gal-8 (red) are shown in the upper left corners.
Figure 4I:
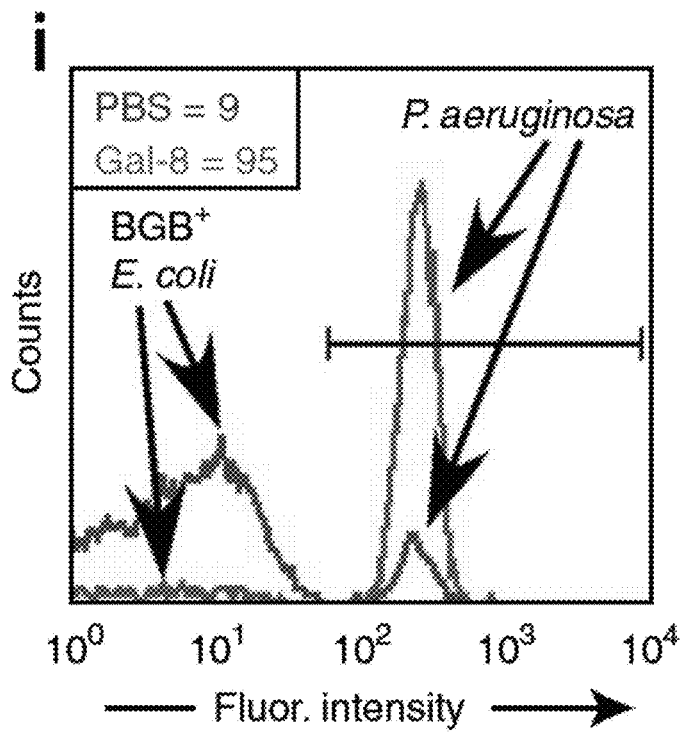
FIG. 4I shows data on the quantification of GFP+ *P. aeruginosa* mixed with BGB+ *E. coli* after incubation with or without 5 μM Gal-8 followed by determination of percentage GFP+ *P. aeruginosa* by flow cytometric analysis in a mixing experiment. Gated counts of GFP+ bacteria treated with PBS (blue) or Gal-8 (red) are shown in the upper left corners.
Figure 4J:
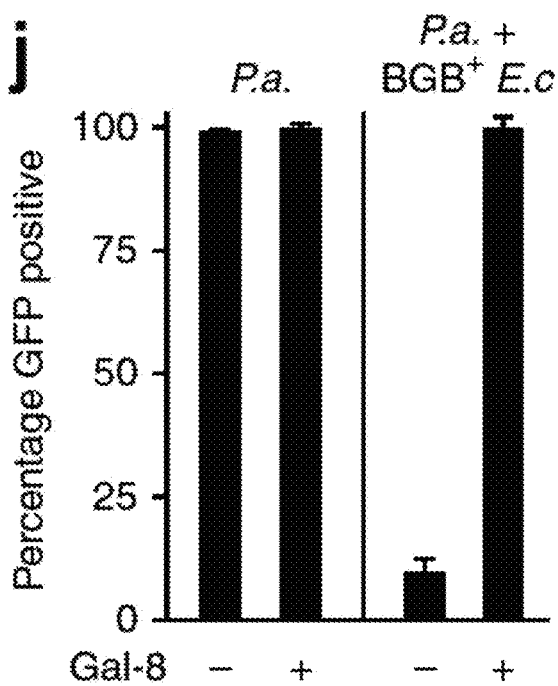
FIG. 4J shows data on the quantification of percentage GFP+ bacteria by flow cytometric analysis after incubation of Gal-8 with either GFP+ *P. aeruginosa* alone (P.a.) or GFP+ *P. aeruginosa* mixed with BGB+ *E. coli* (P.a. +BGB+ E.c.).
Figure 5A:
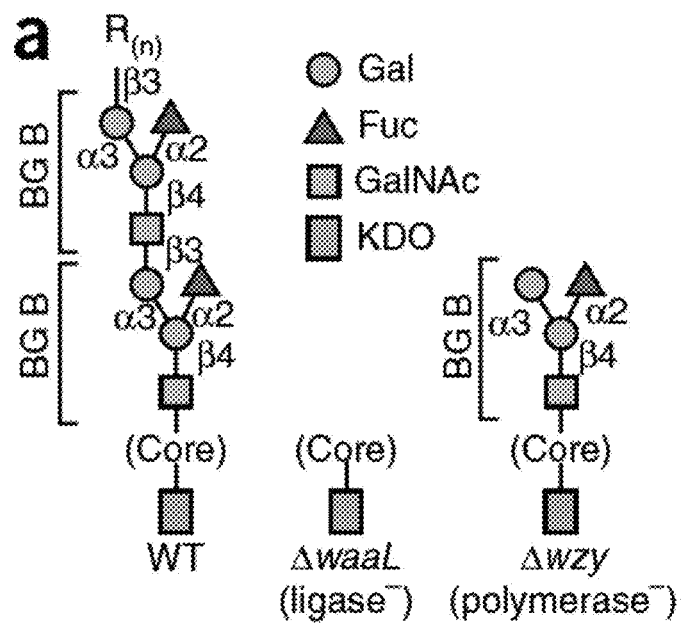
FIG. 5A is a schematic illustration of O antigen structures on WT BGB+ *E. coli* and ΔwaaL and Δwzy mutants of BGB+ *E. coli* lacking a complete O antigen.
Figure 5B:
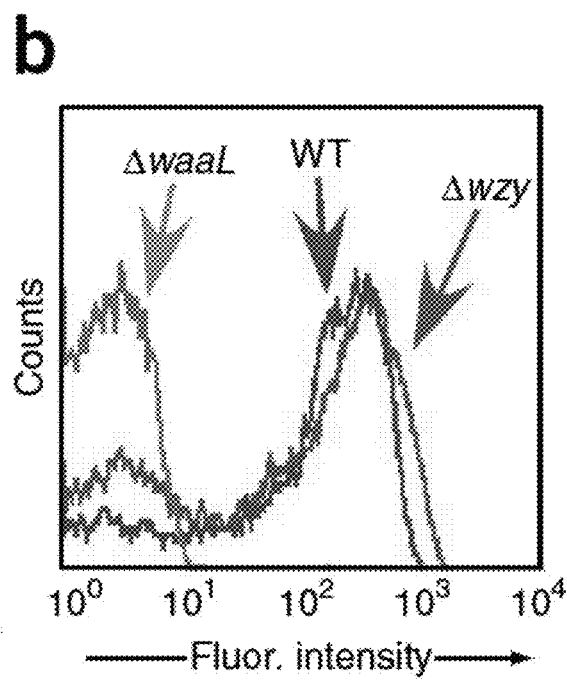
FIG. 5B shows flow cytometric analysis of galectin binding after incubation of BGB+, ΔwaaL and Δwzy *E. coli* with ~0.1 μM Gal-8.
Figure 5C:
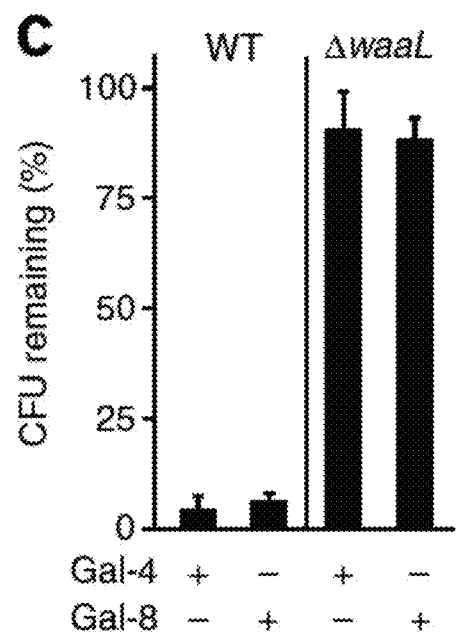
FIG. 5C shows data after incubation of WT and ΔwaaL mutant *E. coli* with 5 μM Gal-4 or Gal-8, as indicated. Viable bacteria were quantified by dilution plating; n=3 experiments; one representative experiment in duplicate over two dilutions shown; error bars represent means±s.d.
Figure 5D:
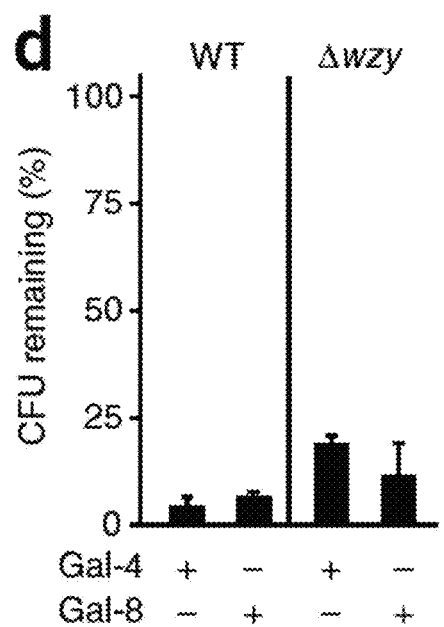
FIG. 5D shows data after incubation of WT and Δwzy mutant *E. coli* with 5 μM Gal-4 or Gal-8, as indicated.

The ability of the blood group-binding domain of Gal-4 and Gal-8 to independently kill $BGB^+$ *E. coli* (FIG. 3a,c,e) suggested that Gal-4 and Gal-8 might specifically kill $BGB^+$ *E. coli*. To test this, whether Gal-4 and Gal-8 recognize strains of *E. coli* that fail to express the blood group B-related antigen was examined. Although both Gal-4 and Gal-8 recognize $BGB^+$ *E. coli*, they did not substantially bind or affect the viability of BGB– *E. coli* (FIG. 4a-c and data not shown). In addition, Gal-4 and Gal-8 did not recognize or kill the Gram-negative, BGB– species *Klebsiella pneumoniae* and *Pseudomonas aeruginosa*, and they neither bound nor altered the viability of Gram-positive *Staphylococcus aureus* (FIG. 4d-g and data not shown). We next asked whether Gal-8 specifically kills $BGB^+$ *E. coli* in a mixed population of $BGB^+$ and BGB– bacteria. We incubated $GFP^+$ BGB– *P. aeruginosa* with Gal-8 to determine whether Gal-8 altered GFP expression or viability. Gal-8 failed to alter GFP expression (FIG. 4h) or viability, allowing us to discriminate between GFP+ *P. aeruginosa* and BGB+ *E. coli* within a mixed population. To examine whether Gal-8 specifically kills BGB+ *E. coli*, various ratios of BGB+ *E. coli* to GFP+ *P. aeruginosa* were incubated with or without Gal-8. Even at a 4:1 ratio of BGB+*E. coli*:GFP+*P. aeruginosa*, Gal-8 selectively eliminated the GFP− BGB+ *E. coli* (FIG. 4*i,j*). Furthermore, defined mutations that prevent synthesis of the blood group antigen formation on BGB+ *E. coli* (ΔwaaL) prevented recognition and killing by Gal-4 and Gal-8, whereas bacteria carrying mutations that allow formation of at least one repeat of the blood group antigen (Δwzy) remained sensitive to Gal-4 and Gal-8 (FIG. 5*a-d*), further illustrating the specificity of Gal-4 and Gal-8 for the blood group B antigen. Of note, lactose, but not sucrose, prevented Gal-4 and Gal-8 killing. Notably, although both Gal-4 and Gal-8 recognized BGB+ human erythrocytes, neither affected the membrane integrity of these cells, which indicates that the killing activity of Gal-4 and Gal-8 not only shows antigen specificity but also uniquely targets prokaryotes. Furthermore, Gal-4- and Gal-8-induced killing of BGB+ *E. coli* did not represent a simple agglutination-associated reduction in colony-forming unit (CFU) counts, as Gal-4 and Gal-8 bound BGB+ *E. coli* at 4° C. but did not alter viability. In addition, both Gal-1 and human BGB-specific antibodies recognized and agglutinated BGB+ *E. coli* at high concentrations, yet failed to affect CFU counts of BGB+ *E. coli* after incubation with the bacteria.

Figure 6A:
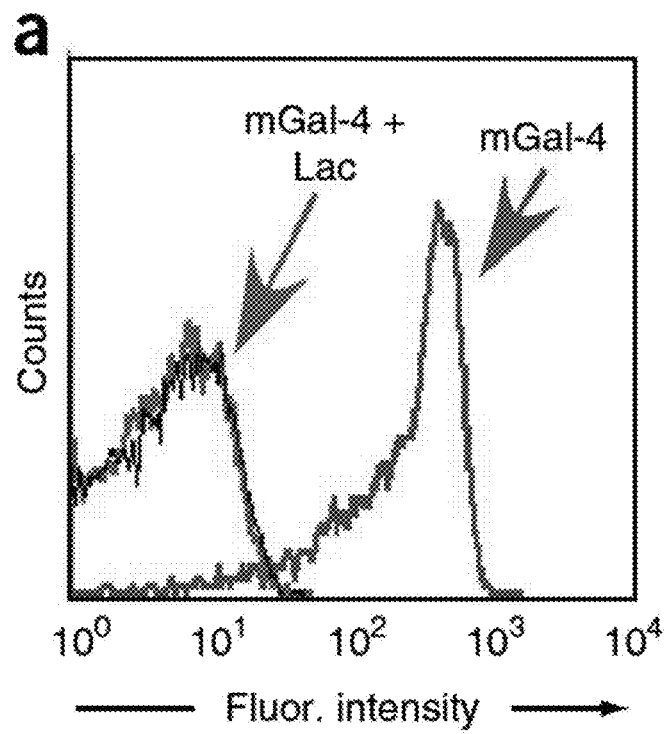
FIG. 6A shows flow cytometric analysis of BGB+ *E. coli* counts after incubation of BGB+ *E. coli* with ~0.1 μM mouse Gal-4 (mGal-4) with or without lactose.
Figure 6B:
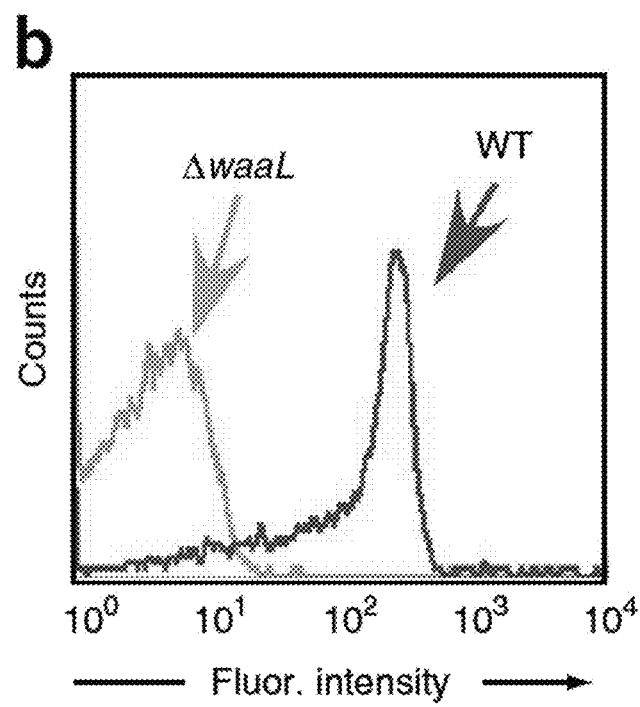
FIG. 6B shows flow cytometric analysis of galectin binding after incubation of BGB+ and ΔwaaL *E. coli* with ~0.1 μM mGal-4.
Figure 6C:
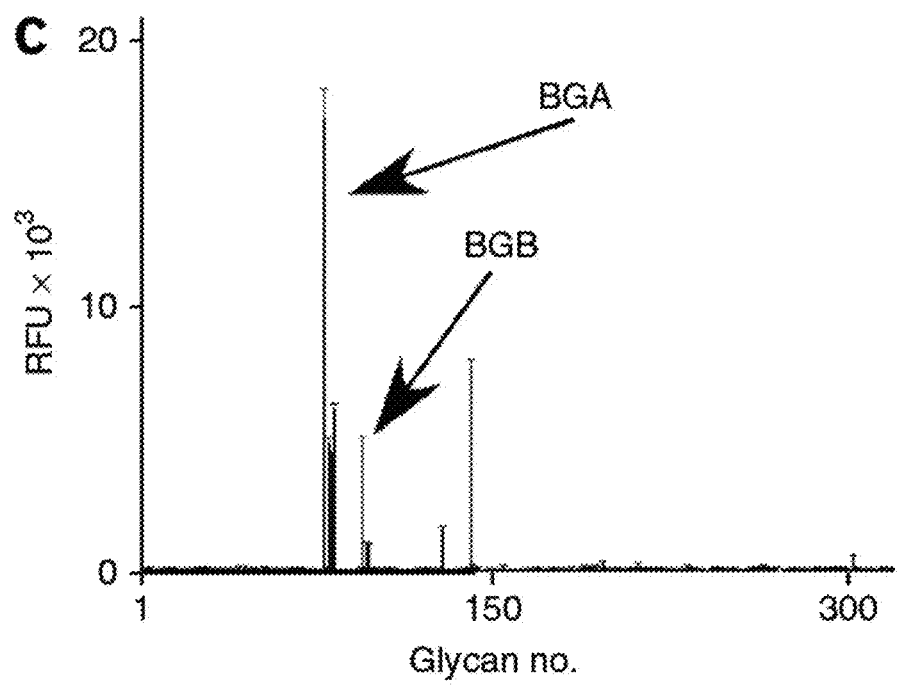
FIG. 6C shows mGal-4 binding to the Consortium for Functional Glycomics glycan microarray at 20 μg ml-1 (0.5 μM).
Figure 6D:
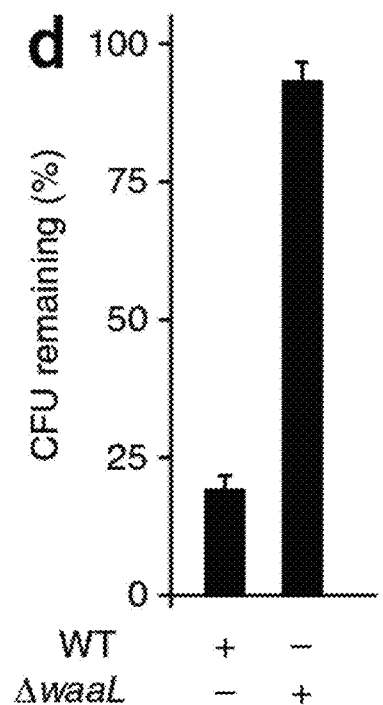
FIG. 6D shows data on the quantification of WT BGB+ and ΔwaaL mutant *E. coli* after incubation with ~5 μM mGal-4. Viable bacteria were quantified by dilution plating; n=3 experiments; one representative experiment in duplicate over two dilutions is shown; error bars represent means±s.d.

Mice we used to test whether similar activities occur in vivo. Whether the mouse galectin-4 (Gal-4) possesses a similar ability to bind and kill BGB+ *E. coli* to human Gal-4 was examined. Recombinant mouse Gal-4 recognized BGB+ *E. coli*, and the recognition was inhibited by both lactose (FIG. 6*a*) and thiodigalactoside, a nonmetabolizable inhibitor of galectins. Furthermore, mouse Gal-4 recognition of BGB+ *E. coli* seemed to be specific to the BGB antigen, as mouse Gal-4 failed to recognize the ΔwaaL mutant (FIG. 6*b*), similar to human Gal-4. Mouse Gal-4 also showed high binding of blood group antigens on the glycan microarray (FIG. 6*c*). Of note, mouse Gal-4 recognition of BGB+ *E. coli* resulted in a substantial reduction in viability, which seemed to be specific to BGB antigen binding, as mouse Gal-4 failed to alter the viability of the ΔwaaL mutant (FIG. 6*d*), and Gal-4-mediated killing was inhibited by thiodigalactoside. However, mouse Gal-4-mediated killing was less potent when compared to human Gal-4, possibly owing to the reduced affinity of mouse Gal-4 for BGB when compared to BGA (FIG. 6*c,d*).

Example 4

Galectins Specifically Kill BGB+ Bacteria In Vivo

Figure 6E:
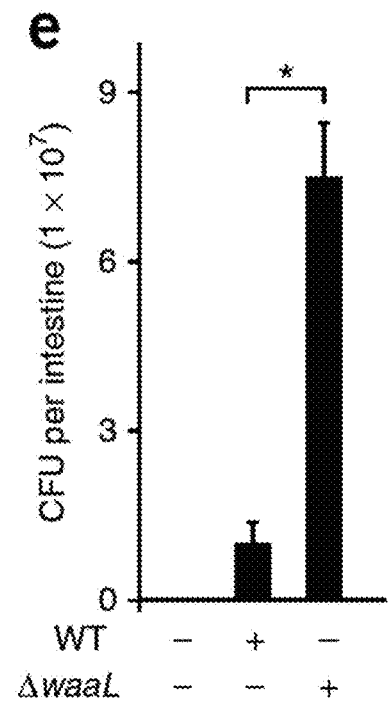
FIG. 6E shows data on the quantification of the number of viable bacteria in the intestine of live, antibiotic-treated mice fed PBS, WT BGB+ or ΔwaaL mutant *E. coli*. The mice were killed 24 h after feeding, and bacteria were quantified by dilution plating. *P=0.049.
Figure 6F:
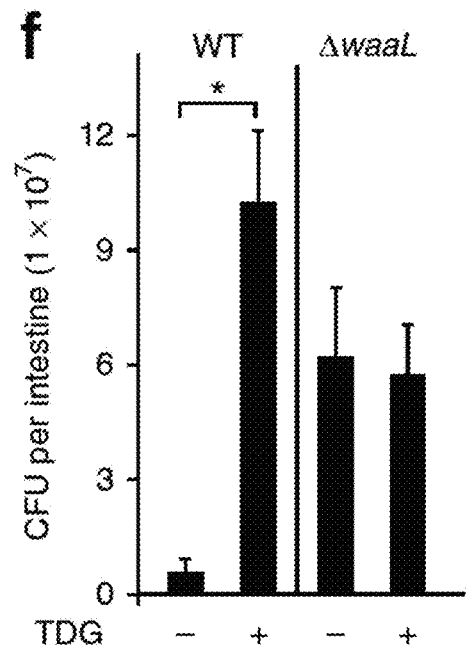
FIG. 6F shows data on the growth of WT and ΔwaaL mutant BGB+ *E. coli* in the presence and absence of thiodigalactoside (TDG). *P=0.008.

The selective killing of BGB+ *E. coli* by mouse Gal-4 suggests that the ΔwaaL mutant should show better growth in vivo as a result of the inability of endogenous galectins to bind and kill these bacteria, whereas BGB+ *E. coli* should be limited in their growth owing to killing by endogenous Gal-4 and Gal-8. It has been shown that Gal-4 and Gal-8 are the only intestinal proteins that detectably bind β-galactosides, but Gal-4 and Gal-8 double-knockout mice are not available, and such mice may not be viable. Thus, to specifically test the physiological functions of these intestinal galectins, wild-type (WT) mice were fed with BGB+ *E. coli* or ΔwaaL mutant *E. coli*. In this in vivo model, mice were treated with streptomycin to deplete endogenous bacteria followed by feeding the mice with the WT and ΔwaaL mutant strains of bacteria. The number of WT bacteria detected was significantly lower in vivo compared to the ΔwaaL mutant (FIG. 6*e*), although both types of bacteria showed equal growth kinetics in vitro, which implicated a possible galectin-mediated process in vivo. The few bacteria isolated from mice inoculated with WT bacteria were positive for BGB antigen. Similarly, bacteria isolated after introduction of the ΔwaaL mutant were negative for the BGB antigen, indicating that the bacteria examined reflected those used during the inoculation. To test the potential role of galectins in the observed difference in growth of the two types of bacteria, BGB+ *E. coli* or ΔwaaL *E. coli* were incubated with or without the inclusion of thiodigalactoside in vivo. Although thiodigalactoside failed to alter the growth of BGB+ *E. coli* or ΔwaaL *E. coli* in the absence of mGal-4, thiodigalactoside significantly increased BGB+ *E. coli* viability in vivo while failing to alter ΔwaaL *E. coli* viability (FIG. 6*f*). These results strongly suggest that endogenous galectins specifically alter the viability of BGB+ *E. coli* in vivo. Although blood group antigens are expressed to some extent in glycosphingolipids and mucins of the gastrointestinal tract, it has been found that they are susceptible to degradation by bacterial-derived glycosidases, and in infants this bacterial-induced degradation of blood group antigens is observed soon after weanin. Thus, it is not likely that host blood group antigens, which are expressed in low amounts, can bind all of the galectins present, as Gal-4 and Gal-8 are highly expressed in the intestinal tract.

Figure 6G:
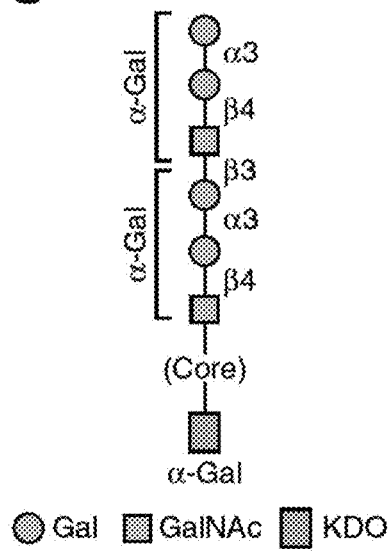
FIG. 6G is a schematic illustration of O antigen structures on α-Gal *E. coli*.
Figure 6H:
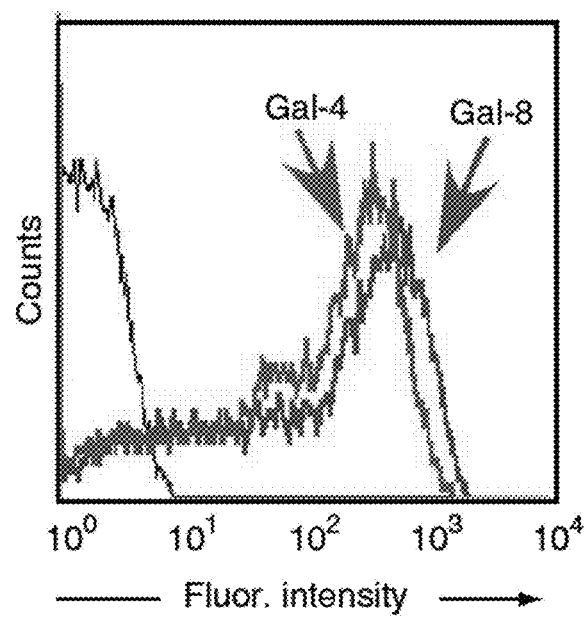
FIG. 6H shows flow cytometric analysis of α-Gal-expressing bacteria after incubation of α-Gal-expressing bacteria with ~0.1 μM human Gal-4 or Gal-8.
Figure 6I:
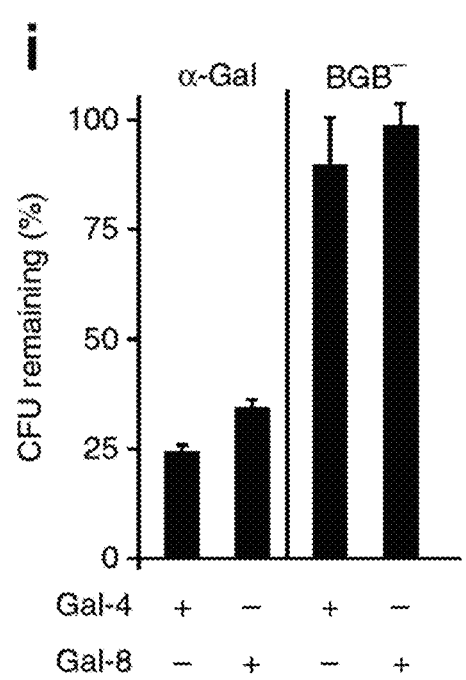
FIG. 6I shows data on the percentage of α-Gal-expressing bacteria and BGB− bacteria remaining after incubation with 5 μM Gal-4 and Gal-8 as compared to PBS-treated control bacteria. Viable bacteria were quantified by dilution plating; n=3 experiments; one representative experiment in duplicate over two dilutions is shown; error bars represent means±s.d.
Figure 7A:
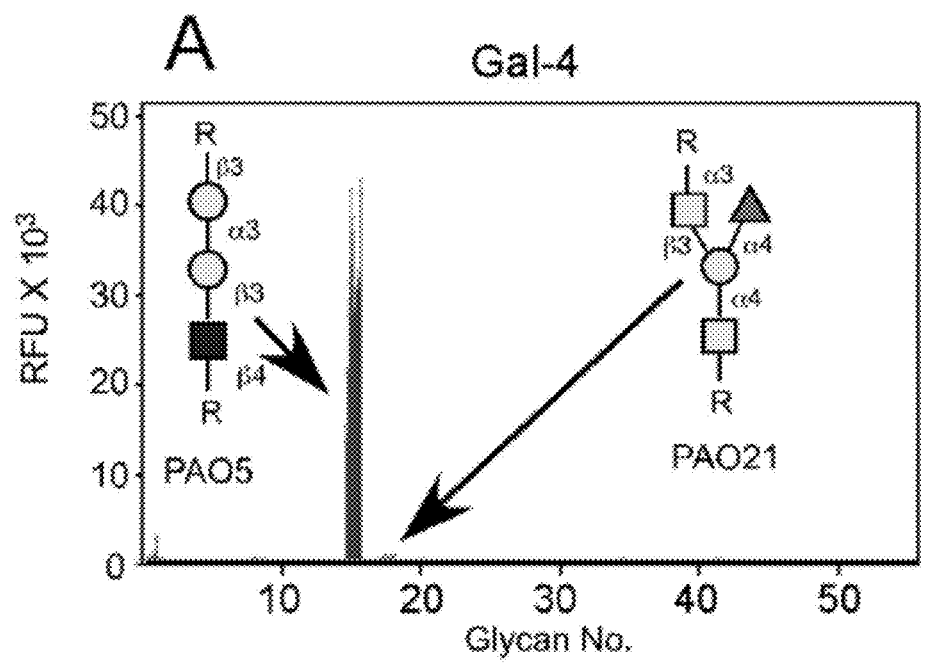
FIG. 7A shows data that suggest Gal-4 and Gal-8 specifically interact with self-like antigens when presented on the MGM. Binding of Gal-4 on the MGM.
Figure 7B:
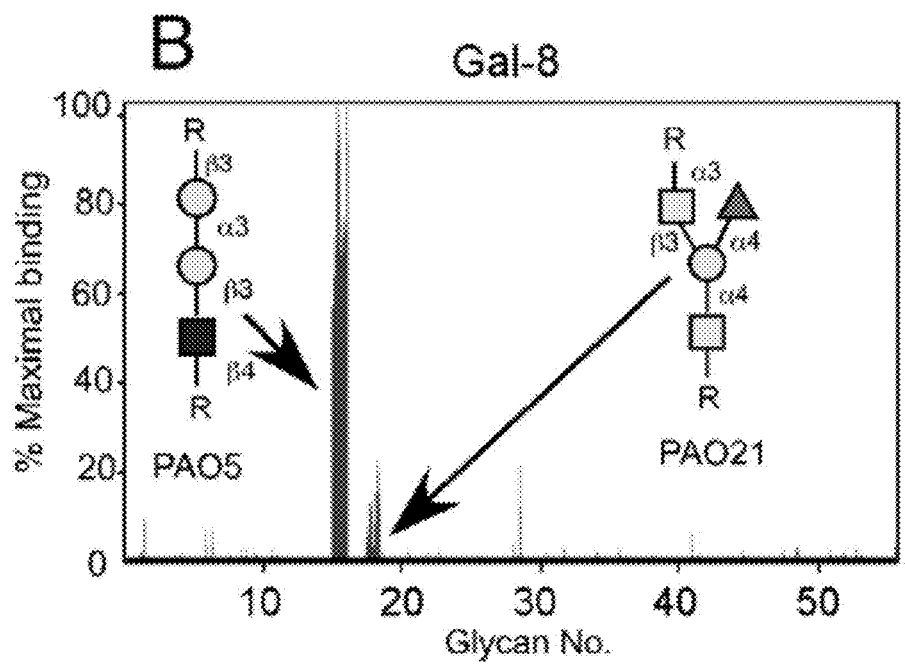
FIG. 7B shows data that suggest Gal-4 and Gal-8 specifically interact with self-like antigens when presented on the MGM. Binding of Gal-8 on the MGM.
Figure 7C:
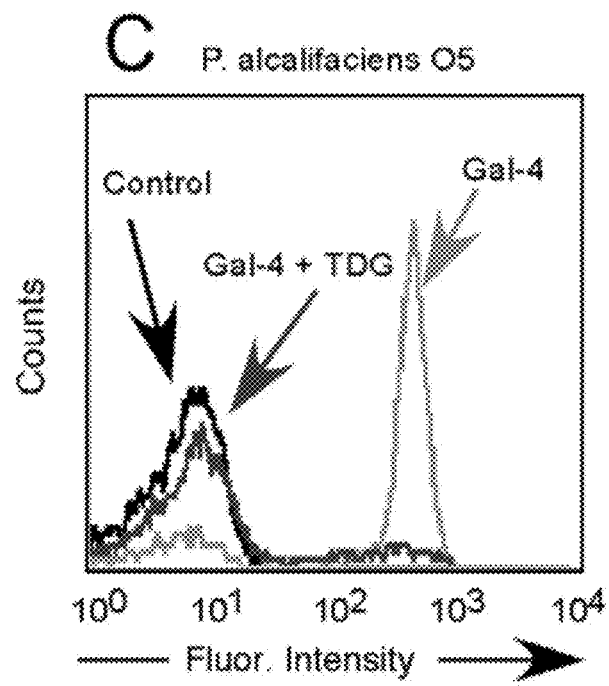
FIG. 7C shows Flow cytometric analysis of *P. alcalifaciens* O5 with Gal-4 or with 20 mM TDG or sucrose as indicated.
Figure 7D:
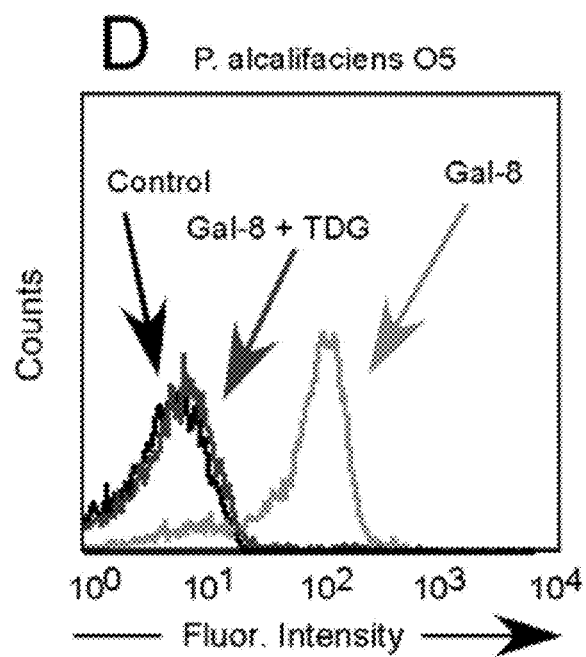
FIG. 7D shows Flow cytometric analysis of *P. alcalifaciens* O5 with Gal-8 or with 20 mM TDG or sucrose as indicated.
Figure 7E:
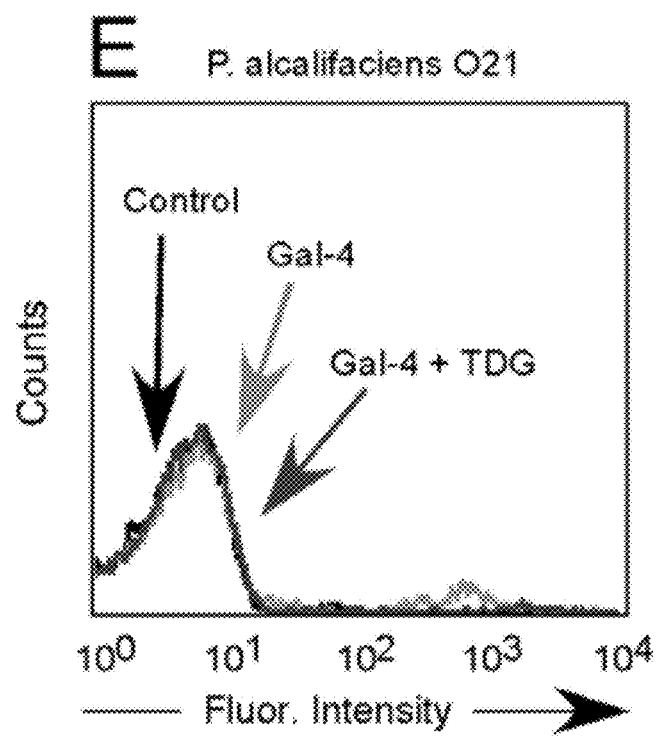
FIG. 7E shows flow cytometric analysis of *P. alcalifaciens* O21 with Gal-4 or with 20 mM TDG or sucrose as indicated.
Figure 7F:
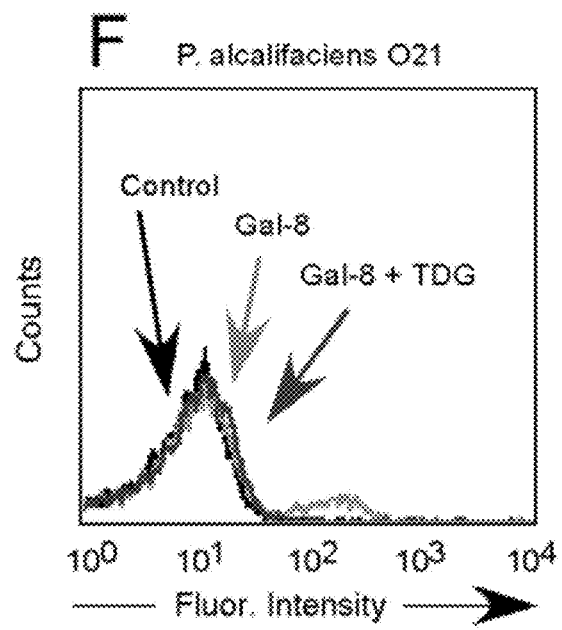
FIG. 7F shows flow cytometric analysis of *P. alcalifaciens* O21 with Gal-8 or with 20 mM TDG or sucrose as indicated.
Figure 7G:
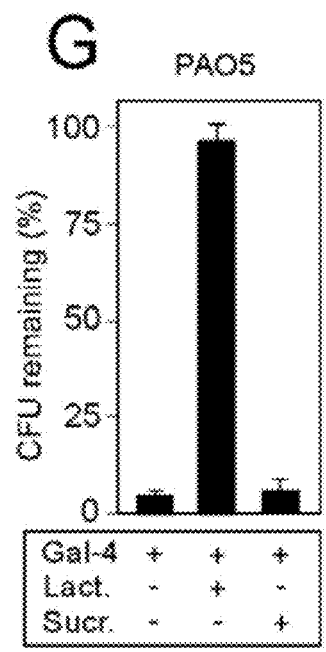
FIG. 7G shows data where *P. alcalifaciens* O5 (G,H,J) or O21 (I) were grown to mid-log phase as indicated followed by addition of Gal-4 or Gal-8 with or without the addition of 20 mM TDG or sucrose. Viable bacteria were quantified by dilution plating.
Figure 7H:
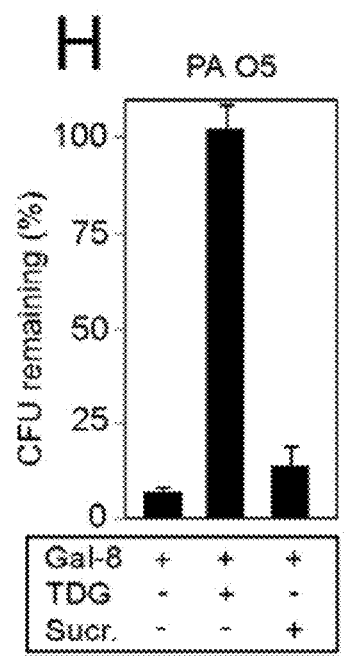
FIG. 7H shows data where *P. alcalifaciens* O5 were grown to mid-log phase as indicated followed by addition of Gal-8 with or without the addition of 20 mM TDG or sucrose. Viable bacteria were quantified by dilution plating.
Figure 7I:
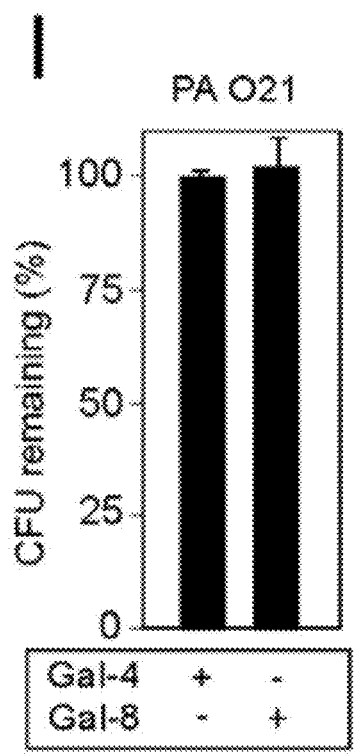
FIG. 7I shows data where *P. alcalifaciens* O21 were grown to mid-log phase as indicated followed by addition of Gal-4 or Gal-8. Viable bacteria were quantified by dilution plating.

Although Gal-4 and Gal-8 seem to kill specifically BGB+ *E. coli*, whether Gal-4 or Gal-8 possess the ability to recognize and kill bacteria expressing other types of blood group antigens remained unknown. To test this, whether Gal-4 and Gal-8 could recognize and kill bacteria expressing the α1-3Gal epitope (α-Gal *E. coli*), a common glycan moiety found in many mammalian species (FIG. 6*g*) was examined. Similar to BGB+ *E. coli*, a-Gal *E. coli* were recognized by Gal-4 and Gal-8 (FIG. 6*h*), and recognition was inhibited by thiodigalactoside. Furthermore, Gal-4 and Gal-8 recognition of α-Gal *E. coli* resulted in a considerable decrease in viability (FIG. 6*i*), although killing of α-Gal *E. coli* by Gal-4 and Gal-8 was reduced when compared to Gal-4- and Gal-8-mediated killing of BGB+ *E. coli*, suggesting a possible reduced binding affinity toward this glycan epitope. Consistent with this, Gal-4 and Gal-8 only recognized α-Gal epitopes on the glycan array when incubated at higher concentrations. Taken together, these results demonstrate that Gal-4 and Gal-8 possess the ability to specifically kill bacteria expressing common blood group-associated mammalian-like antigens.

Example 5

Gal-4 and Gal-8 Recognize a Broad Range of Pathogen Self-Like Antigens

The binding of galectins to lipoligosaccharide (LOS) molecules from a broad range of bacteria were evaluated, including some pathogenic strains, followed by printing of the LOS structure on suitable matrices to generate a microbial glycan microarray (MGM) (FIG. 7). Evaluation of Gal-4 and Gal-8 on the MGM demonstrated specific recognition of only one LOS structure, the LOS of *Providencia alcalifaciens* O5 (PAO5) (FIG. 7A,B). To confirm that Gal-4 and Gal-8 specifically interact with PAO5, it was tested whether Gal-4 and Gal-8 would recognize PAO5 LOS in situ. Gal-4 and Gal-8 not only recognized the PAO5 bacteria, but did not bind PAO21 (FIG. 7C-F), a related strain also printed on the MGM, and whose LOS has a similar composition but different configuration than PAO5. Furthermore, inclusion of thiodigalactoside (TDG), an inhibitor of galectin-carbohydrate interactions, prevented recognition (FIG. 7C-F). Importantly, Gal-4 and Gal-8 not only recognized PAO5, but cause significant death of PAO5 over a similar range of concentrations. Similar to recognition, inclusion of TDG completely prevented Gal-4 or Gal-8 killing of PAO5 (FIG. 7G,H). In addition, Gal-4 and Gal-8 failed to alter the viability of PAO21 (FIG. 7I). Taken together, these results demonstrate that the MGM accurately predicts innate immune factor recognition of pathogens and suggests that PAO5 may be a previously unrecognized target for Gal-4 and Gal-8-mediated immunity.

Figure 8A:
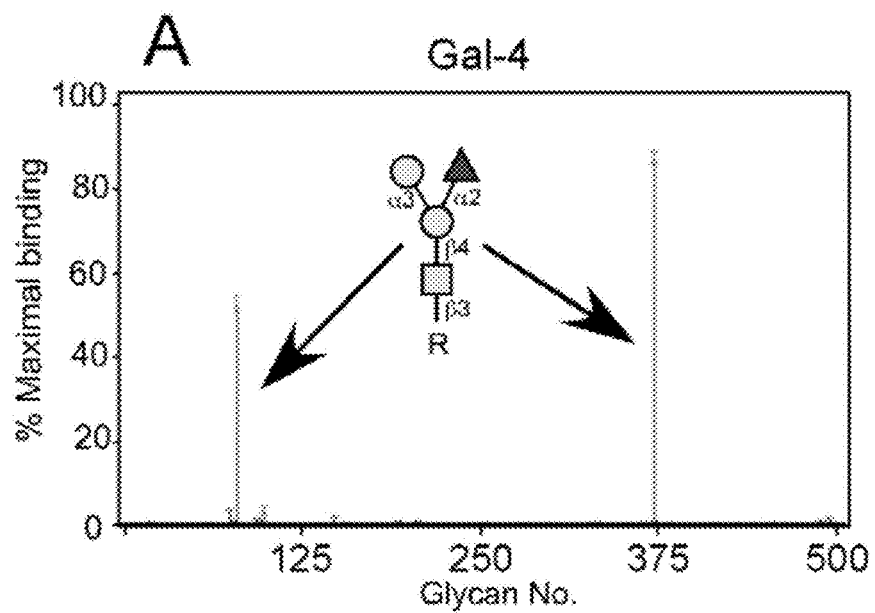
FIG. 8A shows analysis of galectin carbohydrate binding specificity following incubation of 0.2 µM Gal-4 on the glycan microarray. (RFU, relative fluorescence units.) Error bars represent means±s.e.m.
Figure 8B:
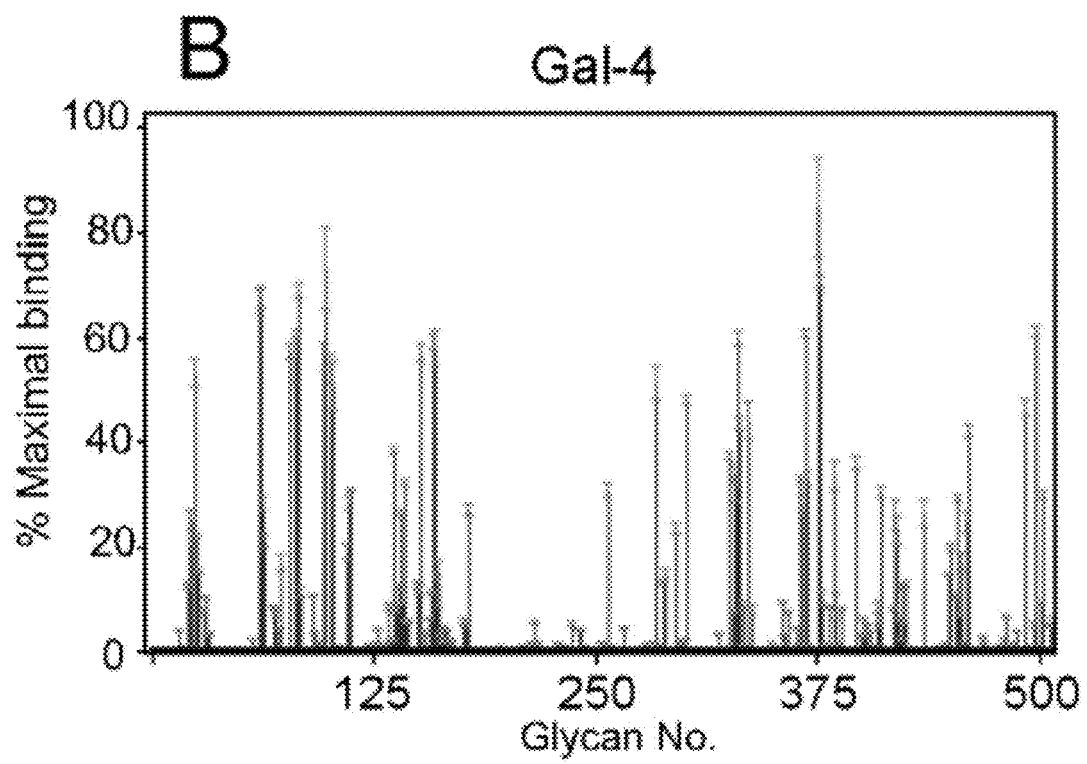
FIG. 8B shows analysis of galectin carbohydrate binding specificity following incubation of 5 µM Gal-4 (B) on the glycan microarray. (RFU, relative fluorescence units.) Error bars represent means±s.e.m.
Figure 8C:
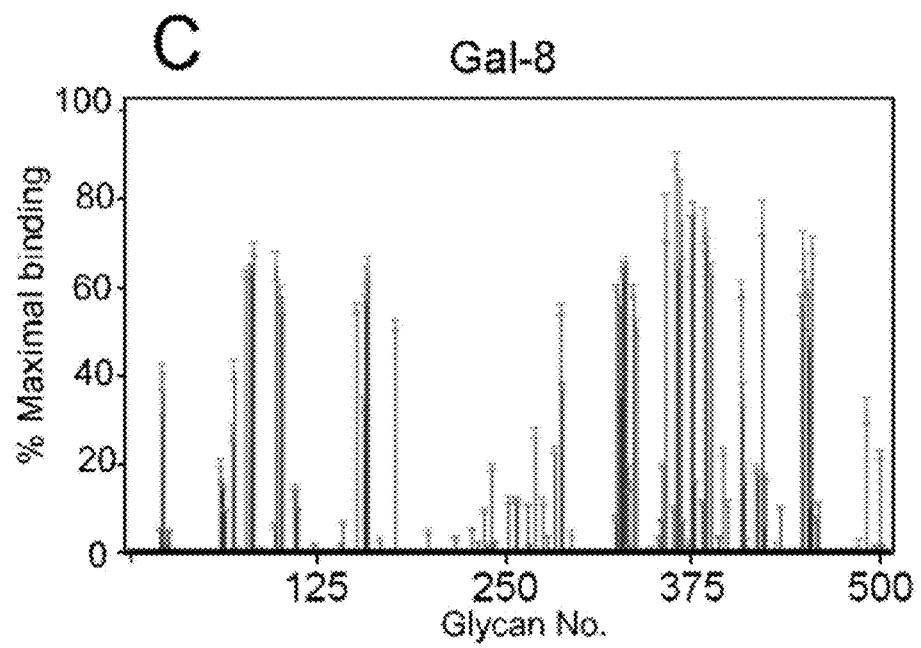
FIG. 8C shows analysis of galectin carbohydrate binding specificity following incubation of 5 µM Gal-8 on the glycan microarray. (RFU, relative fluorescence units.) Error bars represent means±s.e.m.

The distinct recognition of PAO5 by Gal-4 and Gal-8 suggests that PAO5 likely possesses a unique antigenic structure recognized by these innate immune factors. Indeed, careful analysis of the MGM data demonstrated that PAO5 is the only pathogen printed on the MGM that possesses a LOS structure with potential molecular mimicry, the alpha-galactose ($\alpha$-Gal) epitope. However, the ability of Gal-4 and Gal-8 to recognize $\alpha$-Gal epitopes on pathogens with high affinity appears to contrast previous results utilizing the mammalian glycan microarray, and suggests that the unique self-antigen presentation on pathogens may provide high affinity interactions. Indeed, when examined at very low concentrations on the mammalian glycan microarray, Gal-4 displayed significant binding of blood group B antigens (FIG. 8A). However, when examined at higher concentrations, Gal-4 and Gal-8 exhibited a wider range of self-antigen recognition, which included sialylated and terminal lactosamine containing glycans, in addition to the $\alpha$-Gal epitope recognized on the MGM (FIG. 8B,C). These results suggest that, in addition to killing PAO5, Gal-4 and Gal-8 may recognize other pathogens that express alternative self-like antigens.

Figure 8D:
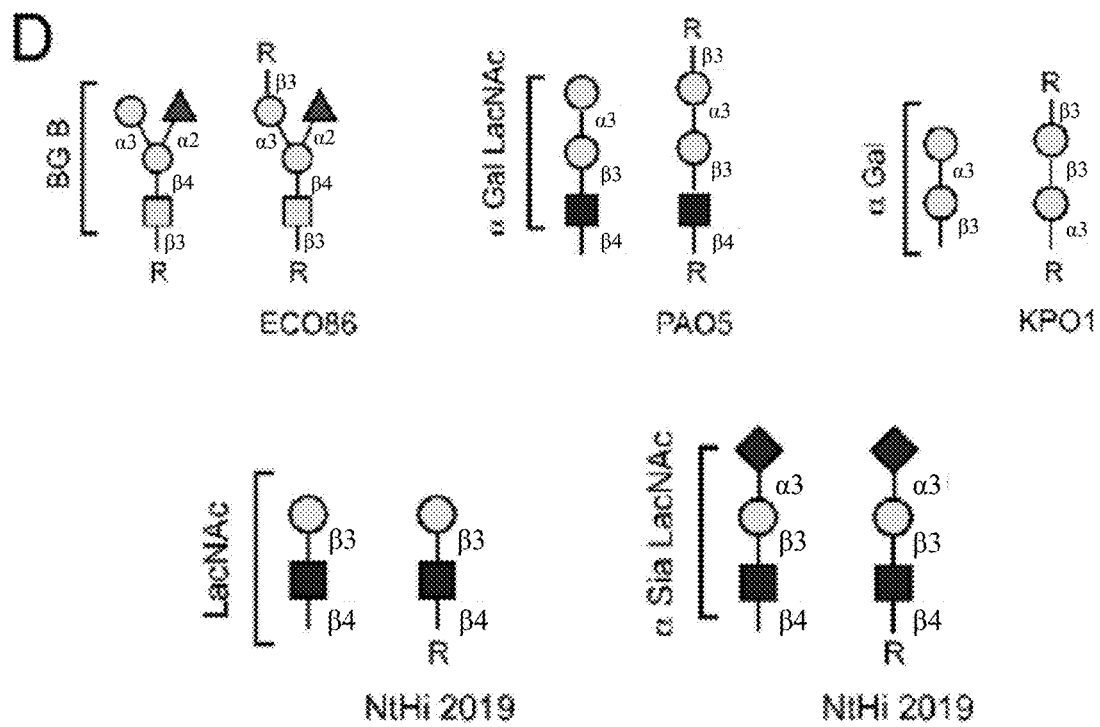
FIG. 8D schematically illustrates representation of glycan structures found on the mammalian glycan array paired with similar structures found on various strains of bacteria as indicated.
Figure 8E:
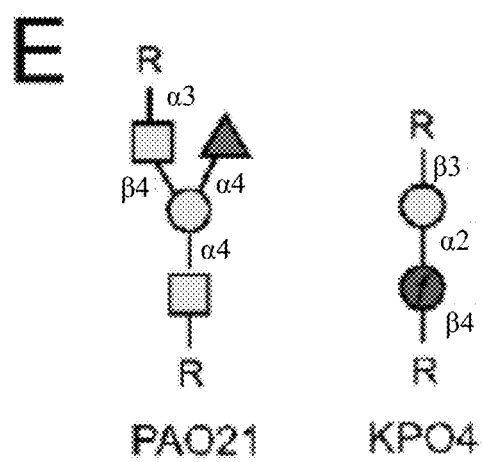
FIG. 8E schematically illustrates representative antigenic structures of related strains that fail to generate self-like antigens.
Figure 8F:
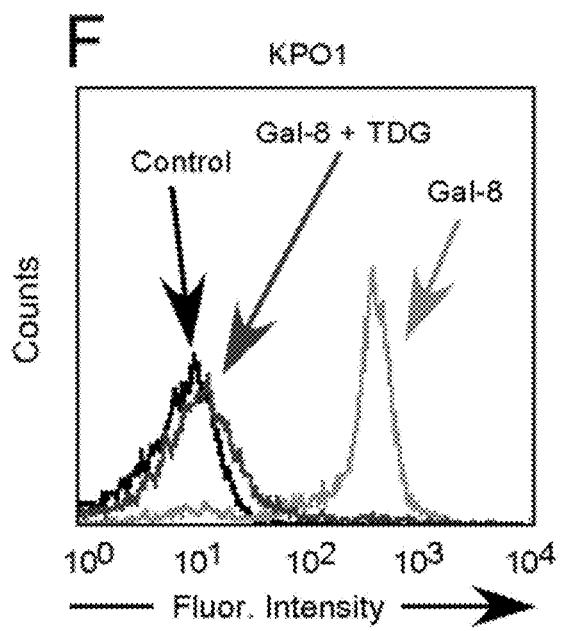
FIG. 8F shows data from flow cytometric analysis of *K. pneumoniae* O1 counts after incubation with Gal-8 with or without inclusion of 20 mM TDG as indicated.
Figure 8G:
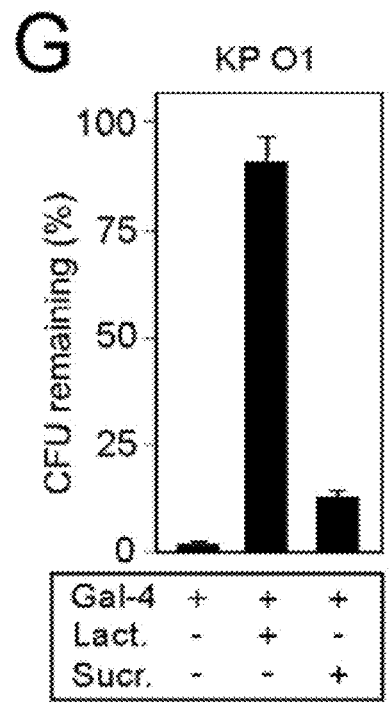
FIG. 8G shows data for *K. pnuemoniae* O1. Bacteria were grown to mid-log phase as indicated followed by addition of Gal-4 with or without the addition of 20 mM TDG or sucrose. Viable bacteria were quantified by dilution plating.
Figure 8H:
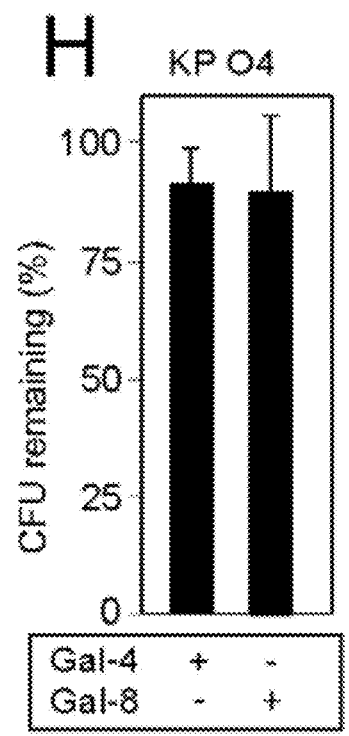
FIG. 8H shows data for *K. pneumoniae* O4 (H). Bacteria were grown to mid-log phase as indicated followed by addition of Gal-4 or Gal-8. Viable bacteria were quantified by dilution plating.

An in silico approach was used in an effort to identify other potential targets which may express self-like antigens similar to those recognized by Gal-4 and Gal-8 on the mammalian glycan microarray. To this end a relatively new searchable database of LOS structures from a diverse range of pathogenic species was utilized. Using this analysis, *Klebsiella pneumoniae* O1 (KPO1) was identified which expresses a nearly identical LOS structure as expressed by PAO5(2) (FIG. 8D). To determine whether in silico predictions of Gal-4 and Gal-8-LOS interactions reflect actual LOS recognition, the potential binding of Gal-4 and Gal-8 toward KPO1 was examined. Gal-4 and Gal-8 recognized KPO1 and inclusion of TDG inhibited recognition (FIG. 8F). Importantly, similar to their inability to recognize PA21, Gal-4 and Gal-8 failed to recognize a related strain of KP, KPO4, which possesses a LOS of similar composition as KPO1, yet fails to generate a self-like antigen. Importantly, incubation of KPO1 with either Gal-4 or Gal-8 resulted in significant loss in cell viability, while Gal-4 and Gal-8 failed to alter the viability of KPO4 (FIG. 8G,H). Furthermore, inclusion of TDG prevented Gal-4 and Gal-8-induced killing (FIG. 8G). These results demonstrate that this in silico approach can identify additional targets for Gal-4 and Gal-8-mediated immunity of pathogens bearing self-like antigens.

Figure 8I:
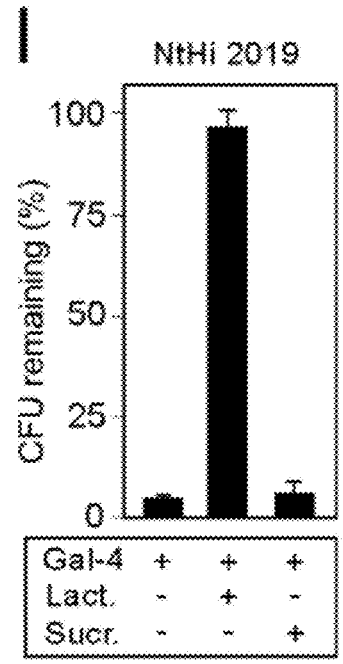
FIG. 8I shows data for NtHi 2019. Bacteria were grown to mid-log phase as indicated followed by addition of Gal-4 with or without the addition of 20 mM TDG or sucrose. Viable bacteria were quantified by dilution plating.
Figure 8J:
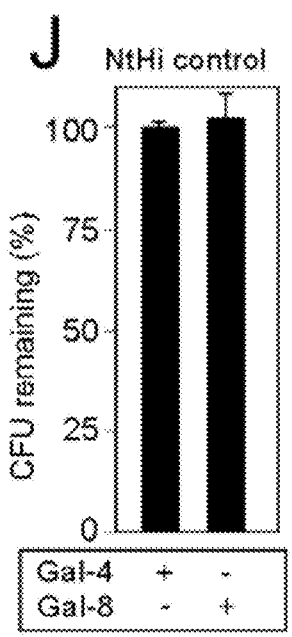
FIG. 8J shows data for NtHi control. Bacteria were grown to mid-log phase as indicated followed by addition of Gal-4 or Gal-8. Viable bacteria were quantified by dilution plating.
Figure 8K:
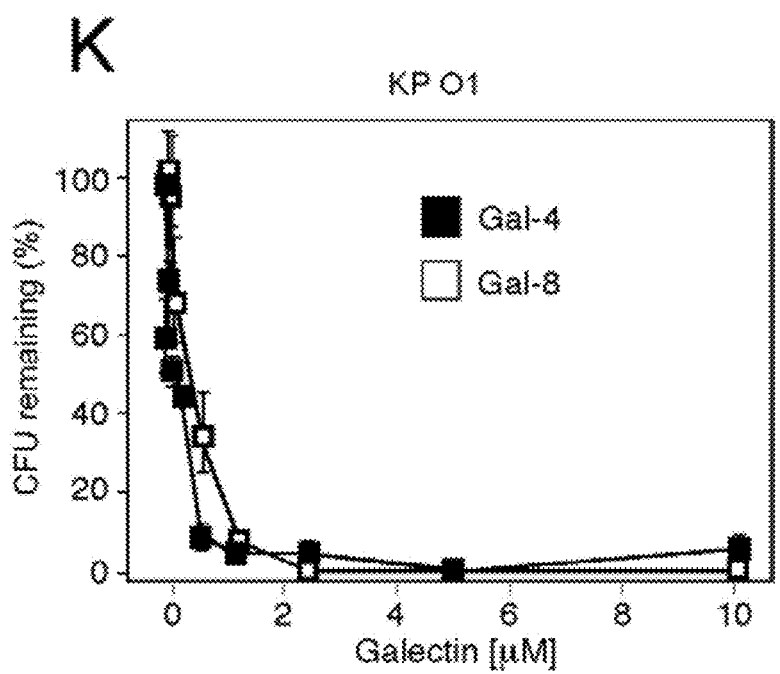
FIG. 8K shows data for *K. pnuemoniae* O1. Bacteria were grown to mid-log phase as indicated followed by addition of Gal-4 or Gal-8. Viable bacteria were quantified by dilution plating.
Figure 9A:
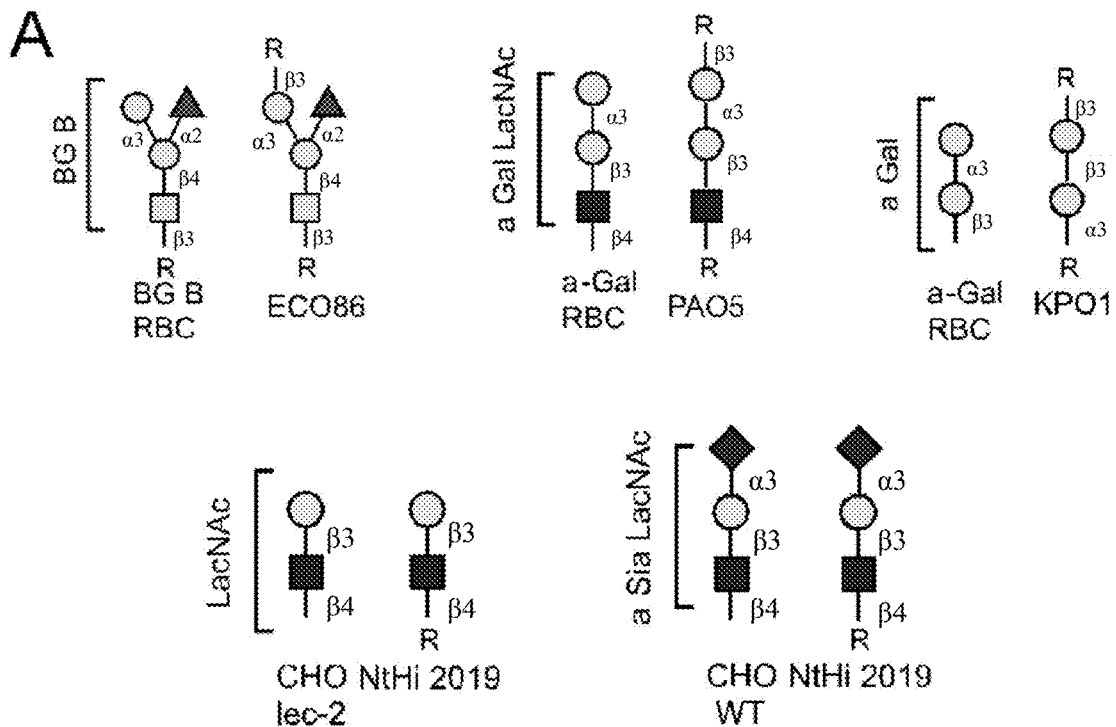
FIG. 9A schematically illustrates representative glycan structures found on various eukaryotic cells as indicated compared to self-like antigenic structures expressed on pathogens.
Figure 9B:
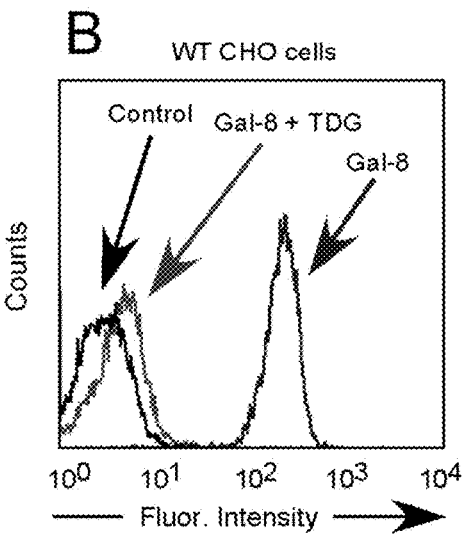
FIG. 9B shows data of flow cytometric analysis of WT CHO cell counts after incubation with Gal-8 with or without inclusion of 20 mM TDG as indicated.
Figure 9C:
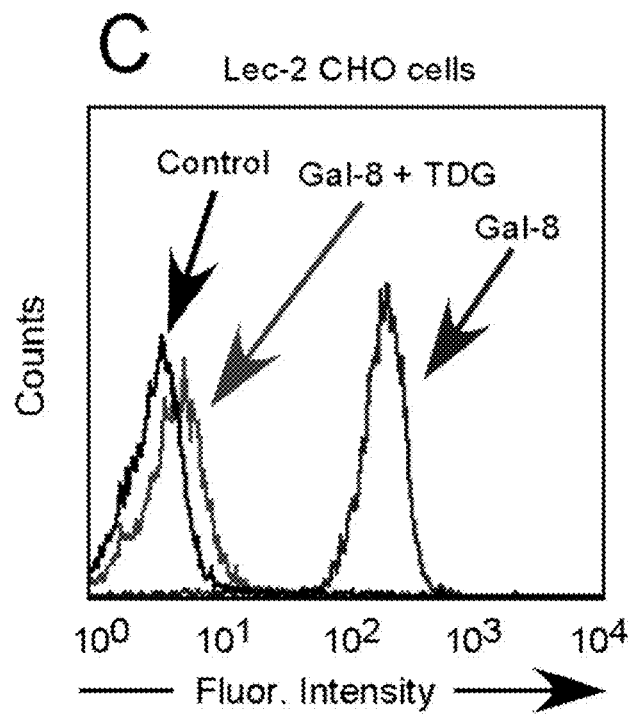
FIG. 9C shows data of flow cytometric analysis of WT Lec2 cell counts after incubation with Gal-8 with or without inclusion of 20 mM TDG as indicated.
Figure 9D:
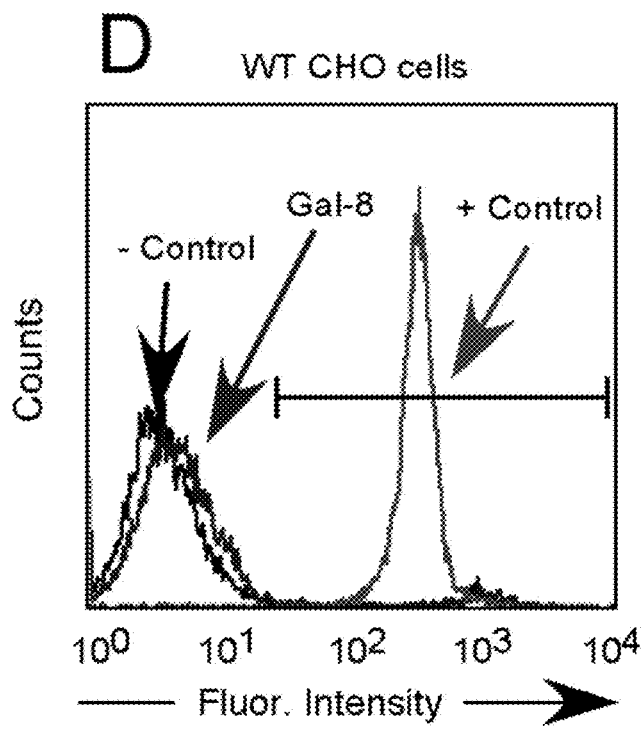
FIG. 9D shows data on the quantification of percent PI positive WT CHO cells after incubation with Gal-8. Incubation with Triton X 100 served as the positive control.
Figure 9E:
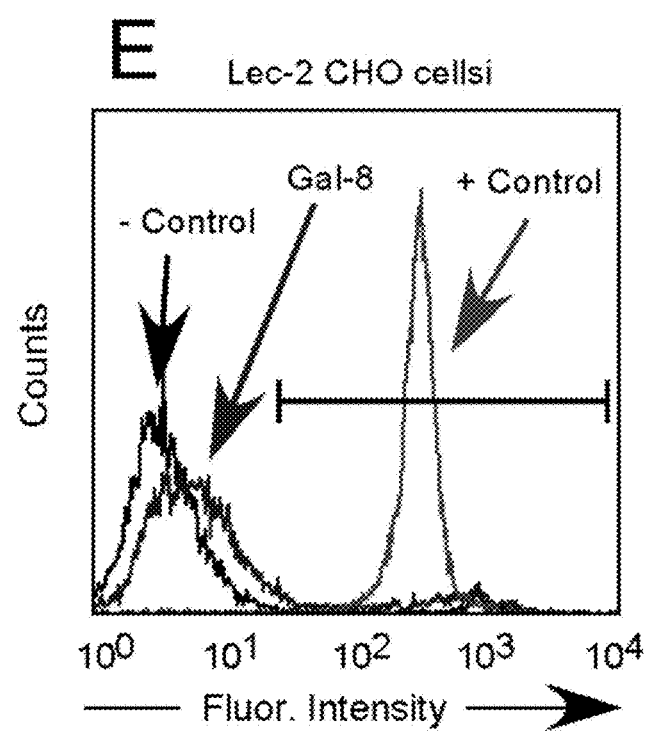
FIG. 9E shows data on the quantification of percent PI positive WT and Lec2 cells (E) after incubation with Gal-8. Incubation with Triton X 100 served as the positive control.
Figure 9F:
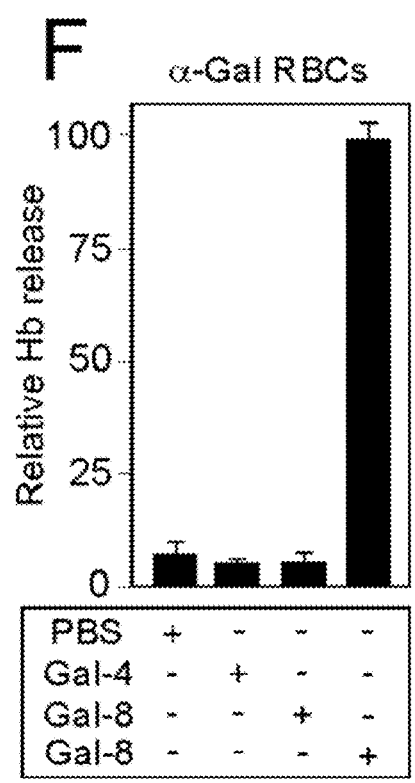
FIG. 9F shows data on the quantification of hemoglobin release from murine erythrocytes after incubation with Gal-4 or Gal-8.
Figure 9G:
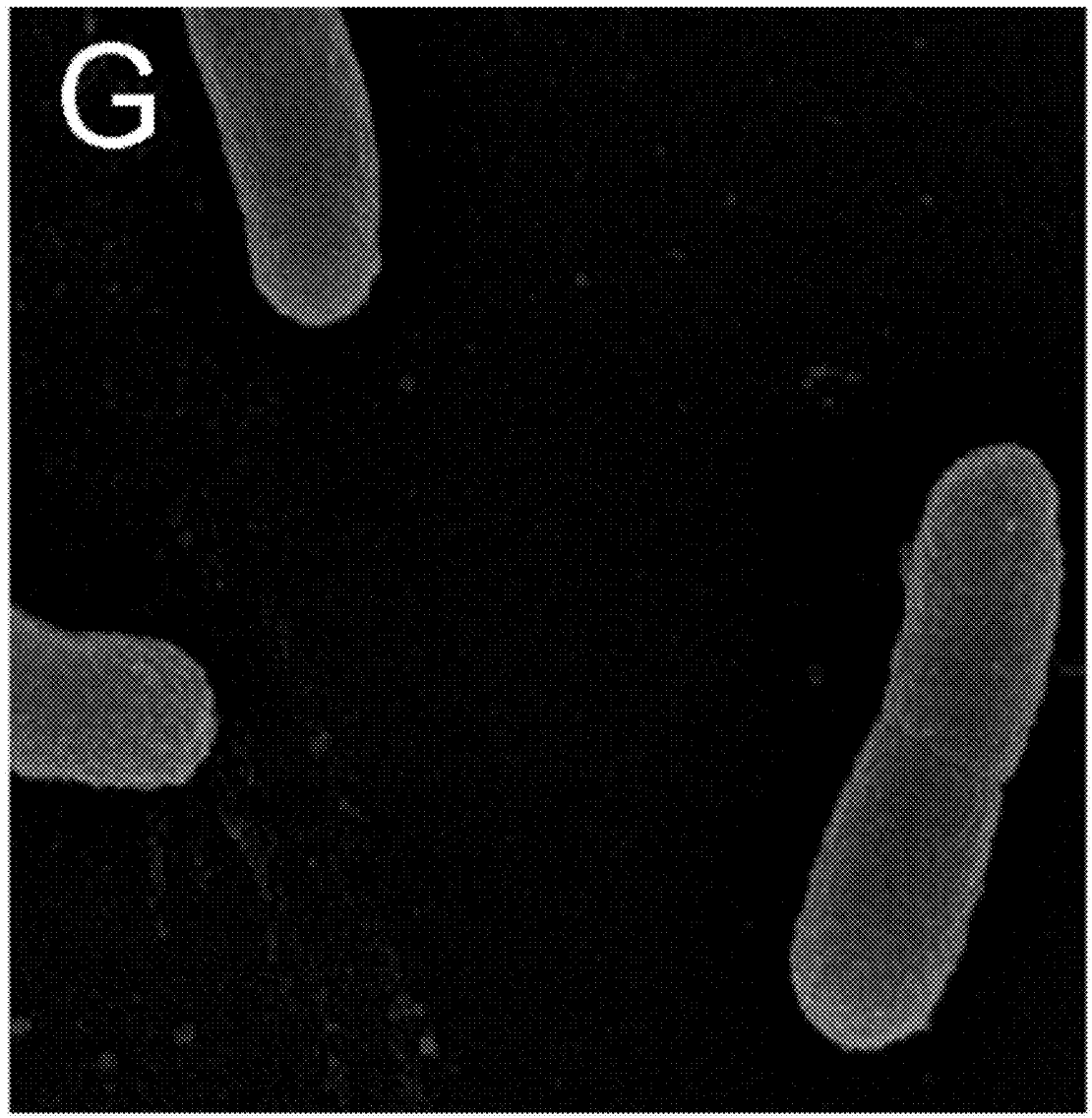
FIG. 9G shows scanning electron microscopy images of *K. pneumoniae* O1 after incubation with PBS for 25 minutes.
Figure 9H:
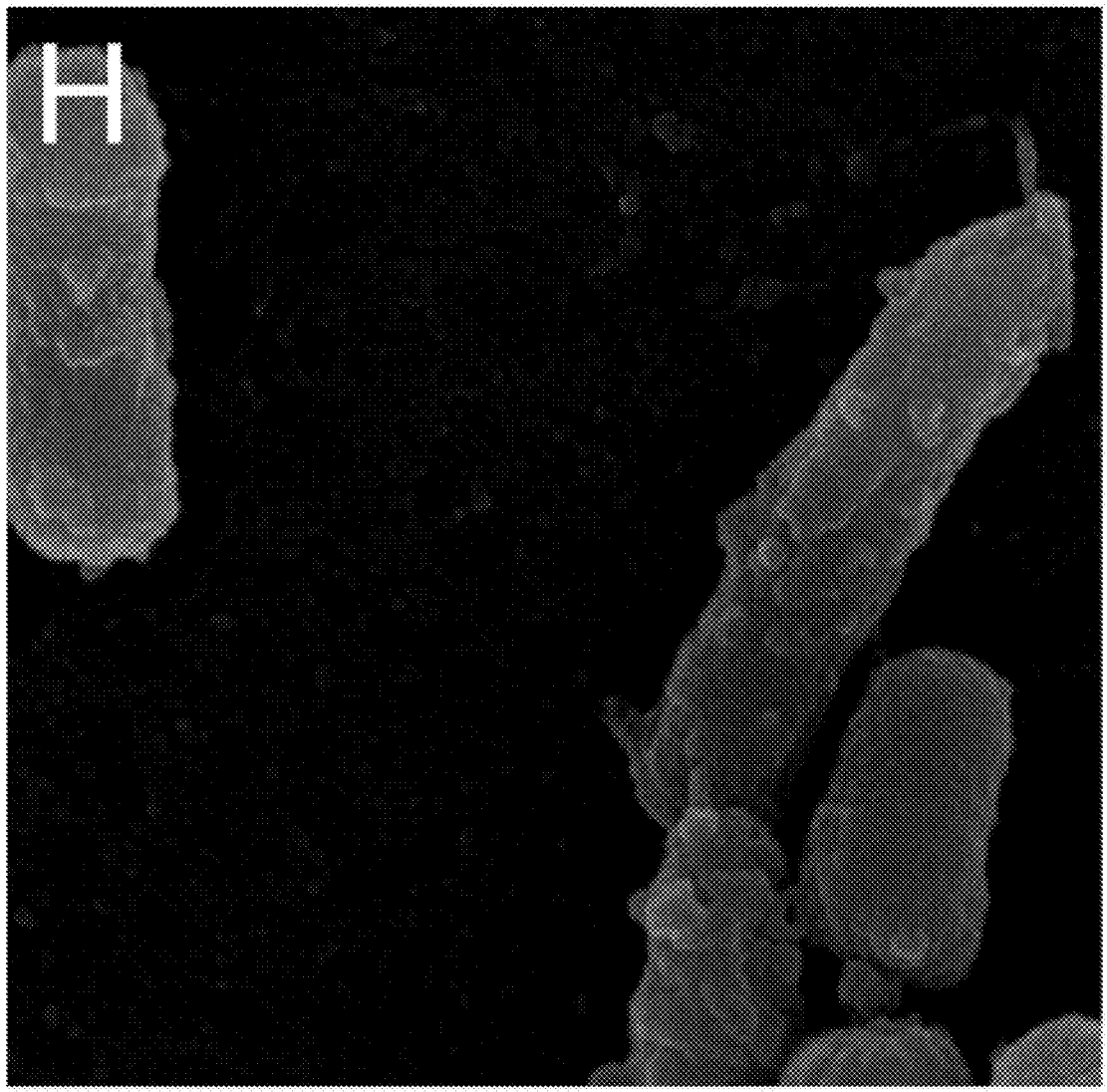
FIG. 9H shows scanning electron microscopy images of *K. pneumoniae* O1 after incubation with Gal-8 (H) for 25 minutes.

As this in silico approach appeared to predict Gal-4 and Gal-8-pathogen interactions, whether Gal-4 or Gal-8 might provide immunity against pathogens which bear other commonly occurring carbohydrate antigens was investigated. To accomplish this, pathogens were searched that generate sialylated carbohydrate antigens, one of the most common monosaccharide modifications on the surface of mammalian cells. In silico analysis identified a nontypeable *Haemophilus influenzae* (NTHi) 2019 as a pathogen that expresses both terminal sialylated and lactosamine antigens. Consistent with the predicted recognition based on the carbohydrate binding properties of Gal-4 and Gal-8 on the mammalian glycan microarray and in silico analysis, Gal-4 and Gal-8 displayed significant recognition of NTHi 2019. Furthermore, incubation of Gal-4 and Gal-8 with NTHi 2019 resulted in significant loss of viability (FIG. 8I-K). Inclusion of TDG not only prevented Gal-4 and Gal-8 recognition of NTHi 2019, but also inhibited Gal-4 and Gal-8-induced killing. Importantly, Gal-4 and Gal-8 failed to recognize or kill strains of NTHi that fail to express sialylated and lactosamine related antigens (FIG. 8J). These results demonstrate that Gal-4 and Gal-8 can recognize and kill bacteria expressing sialylated and terminal lactosamine-containing glycans.

Most innate immune lectins and effecter molecules of the adaptive immune system recognize unique determinants that appear to specifically reside on the surface of a targeted pathogen. Indeed, discrimination of self from non-self at the level of ligand recognition by immune factors likely plays a major role in the ability of immunity to specifically target pathogens. However, the ability of Gal-4 and Gal-8 to not only recognize, but to apparently exclusively recognize self-like antigens stands in stark contrast to other innate immune factors and suggests that Gal-4 and Gal-8 may actually induce similar changes, such as loss of membrane integrity, in mammalian cells. However, while Gal-4 and Gal-8 induced significant loss in viability of PAO5, KPO1, and NTHi 2019, incubation of Gal-4 or Gal-8 with murine erythrocytes, wt CHO or Lec 2 CHO cells which express $\alpha$-Gal, sialylated or LacNAc terminal glycans respectively (FIG. 9A), failed to induce any detectable changes in membrane integrity despite their ability to recognize each of these mammalian cells in a carbohydrate dependent fashion (FIG. 9B-F). Importantly, significant changes in membrane architecture accompanied Gal-4 and Gal-8-induced loss of bacterial viability (FIG. 9G-J). Taken together, these results demonstrate that Gal-4 and Gal-8 have an unprecedented ability to discriminate pathogens versus self while recognizing very similar antigenic structures.

Example 6

Gal-7 and Gal-9 Recognize and Kill Selected Strains of Bacteria Expressing Host-Like Antigens In addition to observed killing by the "tandem repeat galectins", galectin-4 and galectin-8, recent data also implicates tandem repeat galectin-9 (Gal-9) as well as "prototypical" galectin-7 (Gal-7) have direct killing activity as innate immune lectins. Both Gal-7, as well as both the N and C CRD domains of Gal-9, demonstrate specificity for blood group structures on the glycan microarray of the Consortium for Functional Glycomics. In addition Gal-7 and Gal-9 are able to bind directly to blood group positive *Escherichia coli* as well as blood group-like structures on other bacterial strains shown to be targeted by Gal-4 and Gal-8. Incubation of these bacterial strains with either Gal-7 or the Gal-9 domains results in almost complete loss of viability. In addition, further study of Gal-7 killing has demonstrated a similar kinetics, potency, and changes in bacterial membrane morphology to that observed after incubation with Gal-4 or Gal-8.

Methods

Preparation of Recombinant Human Galectins.

Gal-1, Gal-3, Gal-4, Gal-4 domains, Gal-8, Gal-7, Gal-8 domains and Gal-8 mutants, and Gal-9 were prepared as outlined in Stowell et al., J. Biol. Chem. 283, 10109-10123 (2008) and Stowell et al., Mol. Biol. Cell 20, 1408-1418 (2009) hereby incorporated by reference. Gal-8R69H and Gal-8R233H were generated with appropriate primers as described in Stowell et al., J. Biol. Chem. 283, 20547-20559 (2008) hereby incorporated by reference. Galectins were purified to apparent homogeneity by affinity chromatography on lactosyl-Sepharose (Sigma) as observed by SDS-PAGE. To aid in detection, all galectins were derivatized by addition of EZ-link Sulfo-NHS-LC-Biotin (Sulfosuccinimidyl-6-(biotinamido) hexanoate) (Pierce).

Glycan Microarray Preparation and Analysis.

Glycan microarrays were obtained from the Consortium for Functional Glycomics (http://www.functionalglycomics.org/) that were prepared as described in Blixt, O. et al., Proc. Natl. Acad. Sci. USA 101, 17033-17038 (2004) hereby incorporated by reference.

Flow Cytometric Analysis.

To examine potential binding by each galectin, bacteria were grew to mid-log phase in LB medium (Fisher), and resuspended $1\times10^8$ cells per ml in PBS pH 7.4 with biotinylated Gal-1, Gal-3, Gal-4, Gal-4 domains, Gal-8, Gal-8 domains or mutant Gal-4 at concentrations of ~0.1 µM at 4° C. for 30 min. As a control, bacteria were also incubated with 20 mM lactose (Fisher) along with galectins. After incubation, the bacteria were washed three times and incubated them with Alexa Fluor-488-conjugated streptavidin or Alexa Fluor-633-conjugated streptavidin (Molecular Probes) at 4° C. for 30 min. Bacteria were washed two times and resuspended them in 400 µL PBS for analysis by flow cytometry with a FACSCalibur flow cytometer (BD Biosciences). Results were analyzed with CellQuest software (BD Biosciences).

Growth and Treatment of Bacteria.

E. coli O86 (BGB$^+$ E. coli), were received as well as mutant strains and α-Gal E. coli, from Ohio State University. Clinical reference strains were obtained, including the two blood group-negative strains of E. coli (American Type Culture Collection (ATCC) 25922 and ATCC 35218), K. pneumoniae (ATCC 700603), P. aeruginosa (ATCC 27853) and S. aureus (ATCC 29213) from the Emory University Clinical Microbiology lab. When assaying potential antimicrobial effects of galectins, all bacteria were grown to mid-log phase in LB media (Fisher) and incubated $1\times10^8$ cells per mL with the concentrations of each galectin indicated in the figures for 2 h at 37° C., unless otherwise indicated. After incubation with each respective galectin, the number of viable bacteria were determined by dilution plating and CFU enumeration. 20 mM lactose or sucrose was typically incubated with the galectin for 10 min before incubation with bacteria.

Mixed Population.

To assess the specificity of Gal-8-mediated killing in a mixed population, BGB$^+$ E. coli was mixed with GFP-expressing P. aeruginosa (Supplementary Methods) in a 4:1 ratio. This mixture was incubated in the presence or absence of Gal-8 for 2 h at 37° C. followed by dilution plating for CFU enumeration or flow cytometric examination of percentage GFP-positive cells.

Preparation for Visual Analysis.

Either PBS control or 5 µM Gal-8 at 37° C. was added to BGB$^+$ E. coli grown to log phase. BGB$^+$ E. coli were incubated for 30 min with PBS control or 5 µM Gal-8 at 37° C. 20 mM lactose was added to halt treatment and reduce agglutination. Bacteria were washed one time with PBS and centrifuged at 20,000 g in a table-top centrifuge. Bacteria were resuspended in PBS and added 1 µl of propidium iodide solution (1 in 20 dilution of propidium iodide from Live/Dead viability kit (Invitrogen) to PBS). Bacteria were incubated in the dark at 22° C. for 30 min and visualized by fluorescence microscopy at 100× magnification.

Mouse Studies.

Experiments were conducted in accordance with the guidelines of the Animal Care Committee from the University of Sao Paulo (protocol number 09.1.543.53.5). C57BL/6 specific pathogens-free mice were obtained from the animal facilities of the Faculdade de Ciências Farmacêuticas de Ribeirão Preto, Universidade de São Paulo. For in vivo experiments, mice were treated with streptomycin (5 g 1-1) for 48 h. The mice were then fed with either WT BGB$^+$ or ΔwaaL E. coli with or without addition of thiodigalactoside. After 24 h, the mice were killed and the number of viable bacteria were determined in the intestine by dilution plating and CFU enumeration.

The invention claimed is:

1. A method of treating blood group B positive (BGB+) *Escherichia coli* infections comprising administering an effective amount of recombinant human Gal-4 or Gal-4 C-terminal domain peptide to a subject in need thereof.

2. The method of claim 1, wherein the subject is diagnosed with a blood group B positive *E. coli* infection.

* * * * *

SEQUENCE LISTING

```
<160> NUMBER OF SEQ ID NOS: 4

<210> SEQ ID NO 1
<211> LENGTH: 323
<212> TYPE: PRT
<213> ORGANISM: Homo sapiens

<400> SEQUENCE: 1

Met Ala Tyr Val Pro Ala Pro Gly Tyr Gln Pro Thr Tyr Asn Pro Thr
1               5                   10                  15

Leu Pro Tyr Tyr Gln Pro Ile Pro Gly Gly Leu Asn Val Gly Met Ser
            20                  25                  30

Val Tyr Ile Gln Gly Val Ala Ser Glu His Met Lys Arg Phe Phe Val
        35                  40                  45

Asn Phe Val Val Gly Gln Asp Pro Gly Ser Asp Val Ala Phe His Phe
    50                  55                  60

Asn Pro Arg Phe Asp Gly Trp Asp Lys Val Val Phe Asn Thr Leu Gln
```

```
                65                  70                  75                  80
Gly Gly Lys Trp Gly Ser Glu Glu Arg Lys Arg Ser Met Pro Phe Lys
                    85                  90                  95

Lys Gly Ala Ala Phe Glu Leu Val Phe Ile Val Leu Ala Glu His Tyr
                100                 105                 110

Lys Val Val Asn Gly Asn Pro Phe Tyr Glu Tyr Gly His Arg Leu
            115                 120                 125

Pro Leu Gln Met Val Thr His Leu Gln Val Asp Gly Asp Leu Gln Leu
130                 135                 140

Gln Ser Ile Asn Phe Ile Gly Gly Pro Leu Arg Pro Gln Gly Pro
145                 150                 155                 160

Pro Met Met Pro Pro Tyr Pro Gly Pro Gly His Cys His Gln Gln Leu
                165                 170                 175

Asn Ser Leu Pro Thr Met Glu Gly Pro Thr Phe Asn Pro Pro Val
            180                 185                 190

Pro Tyr Phe Gly Arg Leu Gln Gly Leu Thr Ala Arg Arg Thr Ile
        195                 200                 205

Ile Ile Lys Gly Tyr Val Pro Pro Thr Gly Lys Ser Phe Ala Ile Asn
    210                 215                 220

Phe Lys Val Gly Ser Ser Gly Asp Ile Ala Leu His Ile Asn Pro Arg
225                 230                 235                 240

Met Gly Asn Gly Thr Val Val Arg Asn Ser Leu Leu Asn Gly Ser Trp
                245                 250                 255

Gly Ser Glu Glu Lys Lys Ile Thr His Asn Pro Phe Gly Pro Gly Gln
            260                 265                 270

Phe Phe Asp Leu Ser Ile Arg Cys Gly Leu Asp Arg Phe Lys Val Tyr
        275                 280                 285

Ala Asn Gly Gln His Leu Phe Asp Phe Ala His Arg Leu Ser Ala Phe
    290                 295                 300

Gln Arg Val Asp Thr Leu Glu Ile Gln Gly Asp Val Thr Leu Ser Tyr
305                 310                 315                 320

Val Gln Ile

<210> SEQ ID NO 2
<211> LENGTH: 136
<212> TYPE: PRT
<213> ORGANISM: Homo sapiens

<400> SEQUENCE: 2

Met Ser Asn Val Pro His Lys Ser Ser Leu Pro Glu Gly Ile Arg Pro
1               5                   10                  15

Gly Thr Val Leu Arg Ile Arg Gly Leu Val Pro Pro Asn Ala Ser Arg
                20                  25                  30

Phe His Val Asn Leu Leu Cys Gly Glu Glu Gln Gly Ser Asp Ala Ala
            35                  40                  45

Leu His Phe Asn Pro Arg Leu Asp Thr Ser Glu Val Val Phe Asn Ser
        50                  55                  60

Lys Glu Gln Gly Ser Trp Gly Arg Glu Arg Gly Pro Gly Val Pro
65                  70                  75                  80

Phe Gln Arg Gly Gln Pro Phe Glu Val Leu Ile Ile Ala Ser Asp Asp
                85                  90                  95

Gly Phe Lys Ala Val Val Gly Asp Ala Gln Tyr His His Phe Arg His
                100                 105                 110

Arg Leu Pro Leu Ala Arg Val Arg Leu Val Glu Val Gly Gly Asp Val
```

```
                    115                 120                 125
Gln Leu Asp Ser Val Arg Ile Phe
    130             135

<210> SEQ ID NO 3
<211> LENGTH: 359
<212> TYPE: PRT
<213> ORGANISM: Homo sapiens

<400> SEQUENCE: 3

Met Met Leu Ser Leu Asn Asn Leu Gln Asn Ile Ile Tyr Asn Pro Val
1               5                   10                  15

Ile Pro Phe Val Gly Thr Ile Pro Asp Gln Leu Asp Pro Gly Thr Leu
                20                  25                  30

Ile Val Ile Arg Gly His Val Pro Ser Asp Ala Asp Arg Phe Gln Val
            35                  40                  45

Asp Leu Gln Asn Gly Ser Ser Met Lys Pro Arg Ala Asp Val Ala Phe
        50                  55                  60

His Phe Asn Pro Arg Phe Lys Arg Ala Gly Cys Ile Val Cys Asn Thr
65                  70                  75                  80

Leu Ile Asn Glu Lys Trp Gly Arg Glu Glu Ile Thr Tyr Asp Thr Pro
                85                  90                  95

Phe Lys Arg Glu Lys Ser Phe Glu Ile Val Ile Met Val Leu Lys Asp
            100                 105                 110

Lys Phe Gln Val Ala Val Asn Gly Lys His Thr Leu Leu Tyr Gly His
        115                 120                 125

Arg Ile Gly Pro Glu Lys Ile Asp Thr Leu Gly Ile Tyr Gly Lys Val
    130                 135                 140

Asn Ile His Ser Ile Gly Phe Ser Phe Ser Ser Asp Leu Gln Ser Thr
145                 150                 155                 160

Gln Ala Ser Ser Leu Glu Leu Thr Glu Ile Ser Arg Glu Asn Val Pro
                165                 170                 175

Lys Ser Gly Thr Pro Gln Leu Pro Ser Asn Arg Gly Gly Asp Ile Ser
            180                 185                 190

Lys Ile Ala Pro Arg Thr Val Tyr Thr Lys Ser Lys Asp Ser Thr Val
        195                 200                 205

Asn His Thr Leu Thr Cys Thr Lys Ile Pro Pro Met Asn Tyr Val Ser
    210                 215                 220

Lys Arg Leu Pro Phe Ala Ala Arg Leu Asn Thr Pro Met Gly Pro Gly
225                 230                 235                 240

Arg Thr Val Val Val Lys Gly Glu Val Asn Ala Asn Ala Lys Ser Phe
                245                 250                 255

Asn Val Asp Leu Leu Ala Gly Lys Ser Lys Asp Ile Ala Leu His Leu
            260                 265                 270

Asn Pro Arg Leu Asn Ile Lys Ala Phe Val Arg Asn Ser Phe Leu Gln
        275                 280                 285

Glu Ser Trp Gly Glu Glu Arg Asn Ile Thr Ser Phe Pro Phe Ser
    290                 295                 300

Pro Gly Met Tyr Phe Glu Met Ile Ile Tyr Cys Asp Val Arg Glu Phe
305                 310                 315                 320

Lys Val Ala Val Asn Gly Val His Ser Leu Glu Tyr Lys His Arg Phe
                325                 330                 335

Lys Glu Leu Ser Ser Ile Asp Thr Leu Glu Ile Asn Gly Asp Ile His
            340                 345                 350
```

```
Leu Leu Glu Val Arg Ser Trp
        355

<210> SEQ ID NO 4
<211> LENGTH: 323
<212> TYPE: PRT
<213> ORGANISM: Homo sapiens

<400> SEQUENCE: 4

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
            195                 200                 205

Ile Leu Leu Ser Gly Thr Val Leu Pro Ser Ala Gln Arg Phe His Ile
    210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
            275                 280                 285

Val Asp Gly Gln His Leu Phe Glu Tyr Tyr His Arg Leu Arg Asn Leu
    290                 295                 300

Pro Thr Ile Asn Arg Leu Glu Val Gly Gly Asp Ile Gln Leu Thr His
305                 310                 315                 320

Val Gln Thr
```